(12) United States Patent
Vergez et al.

(10) Patent No.: US 8,574,626 B2
(45) Date of Patent: *Nov. 5, 2013

(54) OSMOTIC DEVICE CONTAINING AMANTADINE AND AN OSMOTIC SALT

(75) Inventors: Juan A. Vergez, Buenos Aires (AR); Joaquina Faour, Buenos Aires (AR); Ana C. Pastini, Buenos Aires (AR); Guido S. Bigatti, Buenos Aires (AR); Glenn A. Meyer, Wilmington, NC (US); Ethel C. Feleder, Buenos Aires (AR); Marcelo A. Ricci, Buenos Aires (AR); Marcelo A. Coppari, Buenos Aires (AR); Marcelo F. Befumo, Buenos Aires (AR)

(73) Assignee: Osmotica Kereskedelmi és Szolgáltató KFT, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 13/551,755

(22) Filed: Jul. 18, 2012

(65) Prior Publication Data

US 2013/0115249 A1    May 9, 2013

Related U.S. Application Data

(63) Continuation-in-part of application No. 11/287,882, filed on Nov. 28, 2005, now Pat. No. 8,252,331.

(60) Provisional application No. 60/633,319, filed on Dec. 3, 2004.

(51) Int. Cl.
    *A61K 9/24* (2006.01)
(52) U.S. Cl.
    USPC ......................................................... 424/473
(58) Field of Classification Search
    None
    See application file for complete search history.

(56) References Cited

U.S. PATENT DOCUMENTS

| | | |
|---|---|---|
| 3,878,276 A | 4/1975 | Hoernschemeyer |
| 3,977,404 A | 8/1976 | Theeuwes |
| 4,008,719 A | 2/1977 | Theeuwes |
| 4,014,334 A | 3/1977 | Theeuwes |
| 4,034,758 A | 7/1977 | Theeuwes |
| 4,036,227 A | 7/1977 | Zaffaroni |
| 4,077,407 A | 3/1978 | Theeuwes |
| 4,093,708 A | 6/1978 | Zaffaroni |
| 4,777,049 A | 10/1988 | Magruder |
| 5,057,321 A | 10/1991 | Edgren |
| 5,190,763 A | 3/1993 | Edgren |
| 5,192,550 A | 3/1993 | Edgren |
| 5,221,536 A | 6/1993 | Edgren |
| 5,358,721 A | 10/1994 | Guittard |
| 6,004,582 A | 12/1999 | Faour |
| 6,217,905 B1 | 4/2001 | Edgren |
| 6,248,359 B1 | 6/2001 | Faour |
| 6,284,276 B1 | 9/2001 | Rudnic |
| 6,521,255 B2 | 2/2003 | Vergez |
| 6,569,456 B2 | 5/2003 | Faour |
| 6,572,890 B2 | 6/2003 | Faour |
| 6,599,284 B2 | 7/2003 | Faour |
| 6,599,532 B2 | 7/2003 | Faour |
| 6,605,302 B2 | 8/2003 | Faour |
| 6,613,357 B2 | 9/2003 | Faour |
| 2003/0045577 A1 | 3/2003 | Madhat |

FOREIGN PATENT DOCUMENTS

WO    WO/2004/087116 A1    10/2004

*Primary Examiner* — Paul Dickinson
(74) *Attorney, Agent, or Firm* — Rick Matos; Innovar, L.L.C.

(57) ABSTRACT

The osmotic devices of the present invention contain a unitary core comprising a salt of amantadine and an osmotic salt, wherein the two salts have an ion in common. The release rate of the amantadine is a sigmoidal release. The osmotic device includes a semipermeable membrane having a controlled porosity that can be adapted as needed to cooperate with the osmotic salt in providing a predetermined drug release profile. The osmotic salt need not be coated and it is in admixture with the amantadine salt. The osmotic device further includes a drug-containing coat external to the semipermeable membrane. The osmotic device can include one or more additional drugs in the core and/or the drug-containing coat.

72 Claims, 6 Drawing Sheets

US 8,574,626 B2

OSMOTIC DEVICE CONTAINING AMANTADINE AND AN OSMOTIC SALT

CROSS-REFERENCE TO EARLIER FILED APPLICATION

This application is a continuation-in-part of and claims the benefit of U.S. Ser. No. 11/287,882, filed Nov. 28, 2005, now U.S. Pat. No. 8,252,331 issued Aug. 28, 2012, which claims the benefit of U.S. Provisional Application No. 60/633,319 filed Dec. 3, 2004, the entire disclosures of which are hereby incorporated by reference.

FIELD OF THE INVENTION

This invention pertains to an osmotic device containing an active ingredient (drug) and an osmotic salt in the core, wherein the release rate of the active ingredient is reduced and the release profile of the active ingredient is modified by increasing the amount of the osmotic salt in the core. In one embodiment, the osmotic device contains amantadine hydrochloride and sodium chloride in the core. Depending upon the amount of sodium chloride present in the core, the osmotic device is capable of providing a sigmoidal, pseudo-zero order or zero order release of amantadine hydrochloride.

BACKGROUND OF THE INVENTION

Osmotic devices have demonstrated utility in delivering useful active agents such as medicines, nutrients, food products, pesticides, herbicides, germicides, algaecides, chemical reagents, and others known to those of ordinary skill to an environment of use in a controlled manner over prolonged periods of time. Known devices include tablets, pastilles, pills or capsules and others that use osmotic pressure to control the release of the active agent contained in the core of the osmotic device. Some osmotic devices may also include layers comprising one or more materials that are subject to erosion or that slowly dissolve in the environment of use thereby gradually dispensing the active agent.

Osmotic salts that exhibit an osmotic pressure gradient against an external fluid across the semipermeable wall of the osmotic devices have been used in the core of the osmotic devices for long time. U.S. Pat. Nos. 3,977,404, 4,008,719, 4,014,334, 4,034,758, and 4,077,407 to Theeuwes et al., 4,036,227 and 4,093,708 to Zaffaroni et al., describe that the osmotic salts are used mixed with an agent that has limited solubility in the external fluid with the osmotic salt forming a saturated solution containing agent that is osmotically delivered from the device. The osmotic salts are used by homogenously or heterogeneously mixing the osmotic salt or a mixture of them with an active agent, either before they are charged into the reservoir, or by self-mixing after they are charged into the reservoir. In operation, the osmotic salt attract fluid into the device producing a solution of the osmotic salt which is delivered from the device concomitantly transporting undissolved and dissolved agent to the exterior of the device. U.S. Pat. Nos. 6,248,359 and 6,599,532 to Faour, and 6,569,456, 6,572,890, 6,599,284, 6,599,532, 6,605,302, and 6,613,357 to Faour et al., and 6,521,255 to Vergez et al., teaches the osmotic salts will aid in either the suspension or dissolution of the active ingredient in the core. The osmotic salts can be incorporated to the core of the osmotic device to control the release of the active ingredient therefrom. The above referenced disclosures do not disclose that the release rate of the active ingredient is reduced and the release profile of the active ingredient is modified from one order to another or from one shape to another by increasing the amount of the osmotic salt in the core.

The controlled release of active agents from an osmotic device can occur according to many different release profiles: first order, pseudo-first order, zero order, pseudo-zero order, sigmoidal, delayed, constant rate of release, pulsatile and some combinations thereof. Typically, a drug must have a solubility within the range of 50-300 mg/ml in order to be delivered effectively by an osmotic device.

It is generally well known that highly soluble drug salts can be difficult to formulate into osmotic devices. The more soluble they are, generally the more difficult they are to formulate into osmotic devices. This is because the drug salts tend to dissolve too quickly thereby leading to premature release of the drug, load dumping of the drug or rapid rather than controlled release of the drug. According to McClelland et al. (*Pharm. Res.* (1991), 8(1), 88-92), drugs with a water solubility of $\leq 50$ mg/ml should be released by an osmotic device in a controlled manner such that $\geq 95\%$ of the drug load is released according to zero-order kinetics. Drugs with a high water solubility (e.g., $\geq 300$ mg/ml) should be released by an osmotic device in a controlled manner such that only a very small percentage of the drug load is released according to zero-order kinetics. McClelland et al. therefore propose modulation of the drug solubility in an attempt to change the release profile of a drug from first order to zero order. McClelland et al. specifically state that the NaCl must be present in controlled release form as NaCl crystals coated with cellulose acetate butyrate to form mini osmotic pumps. They state, "This pump-in-a-pump design was necessary to prevent the rapid depletion, and large attendant concentration variation, of the solubility modulating agent (sodium chloride) within the diltiazem hydrochloride core tablet environment." Accordingly, McClelland et al. teach that the desired effect provided by sodium chloride cannot be achieved with uncoated sodium chloride crystals. Apparently according to McClelland et al., uncoated sodium dissolves too quickly to decrease the rate of release of diltiazem.

Due to the complexity of interactions occurring within the core of an osmotic device, no generally applicable approach has been developed to control and reduce the rate of dissolution of very water soluble drugs. In fact, some osmotic device excipients accelerate rather than decelerate the rate of drug release.

The use of sodium chloride as an osmagent in an osmotic device is widely known. The art generally teaches that increasing the amount of osmagent results in an increase of osmotic pressure and thereby an increase in the rate of release of drug from the core of the osmotic device. The prior art discloses osmotic devices having a bi-layered or multi-layered core, wherein at least one of the layers is a "push" or "displacement" layer comprising sodium chloride in combination with an osmopolymer or a water swellable polymer. A push layer is generally inert and does not contain drug. The NaCl serves to draw water within the polymer matrix thereby wetting and swelling the polymer.

An osmotic device having a unitary core comprising a pharmaceutically acceptable salt of a drug in combination with sodium chloride and other excipients is known. In particular, the art discloses osmotic devices having a unitary core comprising drugs such as pseudoephedrine hydrochloride (Johnson et al. in U.S. Pat. No. 6,537,573; Faour et al. in U.S. Pat. No. 6,004,582; Hamel et al. in U.S. Pat. No. 4,801,461; Chen et al. in U.S. Pat. No. 5,458,887, U.S. Pat. No. 5,654, 005, and U.S. Pat. No. 5,558,879), venlafaxine hydrochloride (Faour et al. in U.S. Pat. No. 6,352,721), reboxetine methane sulfonate (Seroff et al. in U.S. Pat. No. 6,387,403), carbamazepine (Puthli et al. in U.S. Pat. No. 6,534,090), rofecoxib (Faour et al. in U.S. Pat. No. 6,491,949), cisapride monohydrate (Faour et al. in U.S. Pat. No. 6,004,582), nifedipine (Kettelhoit et al. in U.S. Pat. No. 6,294,201); or other drugs (Chen et al. in U.S. Pat. No. 5,736,159 and U.S. Pat. No. 5,837,379) in combination with sodium chloride and other excipients. The art also discloses osmotic devices having bi-layered or multi-layered cores, wherein one of the layers includes a drug and sodium chloride among other excipients (Wong et al. in U.S. Pat. No. 5,785,994; Kuczynski et al. in U.S. Pat. No. 5,866,164). Osmotic devices having a bi-layered core comprising an active ingredient and sodium chloride in the drug-containing layer are disclosed in U.S. Pat. No. 6,352,721 to Faour, which teaches about three osmotic devices containing a core layer comprising venlafaxine hydrochloride and sodium chloride, cisapride and sodium chloride, and nifedipine and sodium chloride, respectively, U.S. Pat. Nos. 5,674,895, 5,840,754, 5,912,268, 6,124,355, 6,262,115 and U.S. Patent Application No. 20010005728, to Guittard et al., and U.S. Patent Application No. 20010009995 to Gupta et al., which disclose a core layer comprising oxybutynin and sodium chloride, and U.S. Pat. No. 6,387,403 to Seroff et al., which discloses a core layer comprising reboxetine methane sulfonate and sodium chloride. International documents WO03/039519 and WO03/039436 to Vergez et al., disclose osmotic devices comprising bi-layered cores comprising a drug in each layer of the core; drug-layer compositions comprising sodium chloride are exemplified. Osmotic devices having a multi-layered core are disclosed in U.S. Pat. No. 5,785,994 to Wong et al., wherein one of the layers includes a drug, such as diltiazem HCl, and potassium chloride among other excipients. In all above-referenced patents, the osmotic salt is disclosed as an osmagent that increases the osmotic pressure of the core by attracting fluid into the device, and thereby producing a solution or suspension of the active ingredient that is then delivered from the device at increased rate. None of above-referenced patents disclose that the release rate of the active ingredient is reduced and that the release profile of the active ingredient is modified by increasing the amount of the osmotic salt in the core. The weight percentages of sodium chloride and the drug as disclosed in the prior art are highly variable.

However, the art is not consistent regarding use of NaCl in osmotic devices: Ramakrishna et al. (*Pharmazie* (2001), 56(12), 958-962); and Lin et al. (*J. Pharm. Sci.* (2002), 91(9), 2040-2046).

Accordingly, the art in this area is unpredictable, meaning that one cannot predict with certainty, or a priori, whether increasing the amount of sodium chloride in an osmotic pump containing a drug salt will decrease or increase the rate of release of the drug salt. This is particularly true for specific drug salt and osmotic salt combinations.

Amantadine is available commercially in the United States in immediate release tablet form and syrup form under the trademark SYMMETREL™ from Endo Pharmaceutical Co. The administration of amantadine for the treatment of Parkinson's disease, Alzheimer's disease and some types of dementia is well known. As noted in the Physician's Desk Reference 56$^{th}$ Ed. 2002, depression, among other mood disorders, is a known adverse reaction to amantadine therapy. Moreover, amantadine is subject to undesirable interactions with a number of other drugs.

U.S. Pat. Nos. 6,217,905, 5,221,536 and 5,190,763 to Ayer et al. and 5,192,550 and 5,057,321 to Edgren et al. of Alza Corporation disclose bi-layered osmotic device formulations containing an anti-Parkinson's drug such as amantadine. In this embodiment, the core is bi-layered and comprises a drug composition and a push-composition. An osmotic salt such as sodium chloride, potassium chloride, or magnesium chloride can be included in the push-composition.

U.S. Pat. No. 5,358,721 to Guittard et al. of Alza Corporation discloses bi-layered osmotic device formulations containing an anti-viral drug such as amantadine. In this embodiment, the core is bi-layered and comprises a drug composition and a push-composition. An osmotic salt such as sodium chloride, potassium chloride, or magnesium chloride can be included in the push-composition.

U.S. Pat. No. 6,284,276 to Rudnic et al. discloses an osmotic pharmaceutical delivery system comprised of a semipermeable wall that maintains its integrity during pharmaceutical delivery and that has a passage through it, and a composition within the semipermeable wall, wherein the composition is comprised of a pharmaceutical agent of limited solubility, a non-swelling agent that enhances the solubility of the pharmaceutical agent, and a non-swelling osmotic agent. The '276 patent mentions amantadine as a drug that is suitable for use in the osmotic device.

It is known in the field of osmotic devices that changing the release profile of a drug can have an effect upon the clinical benefit observed in a patient to which the osmotic device is administered. Depending upon the drug being administered, the disease or disorder being treated, the observed clinical response in a subject and other considerations, a particular controlled release profile will be preferred in providing an intended clinical benefit. In some situations, a zero order release profile is preferred while in others a first order release profile or a sigmoid release profile is observed.

Osmotic devices manufacture with two or more layers in order to provide a desired release rate profile can be difficult to produce and require specialized manufacturing machinery. Therefore, it would be an improvement in the art to provide a controlled release dosage form that is easily manufactured and produces a desired release rate or release rate profile for a desired soluble or insoluble hydrochloride salt of an active agent by modifying the amount of sodium chloride in the core of the osmotic device.

SUMMARY OF THE INVENTION

The invention provides an osmotic device that release amantadine in a controlled fashion. The rate of release of amantadine decreases with increasing amounts of osmotic salt, such as NaCl, added to the core. The amantadine salt and osmotic salt have an ion in common. The osmotic salt is not coated per se with a release rate controlling coating. The osmotic salt is present in crystalline or powdered form and is included in the core of the osmotic device in admixture with amantadine and other excipients. The core is a non-layered unitary core wherein the ingredients are homogeneously or heterogeneously mixed.

One aspect of the invention provides an osmotic device having a unitary core surrounded by a semipermeable membrane having at least one passageway there through, wherein:

a. the unitary core comprises a mixture of amantadine salt, osmotic salt, and at least one other pharmaceutically acceptable excipient;

b. the osmotic salt is not coated with a release rate controlling coating;

c. the permeability of the semipermeable membrane is adapted to cooperate with the osmotic salt to control the release profile of amantadine salt from the osmotic device;

d. the amantadine salt and osmotic salt have an ion in common; and e. amantadine salt is released according to a first order, a zero-order or pseudo-zero order, or a sigmoidal controlled release profile, optionally wherein release of amantadine salt is delayed for a period of time, when the osmotic device is exposed to an aqueous environment of use.

Another aspect of the invention provides an osmotic device comprising a unitary core surrounded by a semipermeable membrane having at least one passageway there through, wherein:

a) the unitary core comprises a mixture of amantadine salt, osmotic salt, and at least one other pharmaceutically acceptable excipient, and the weight ratio of amantadine salt to osmotic salt ranges from 2:1 to 30:1;

b) the osmotic salt is not coated with a release rate controlling coating;

c) the permeability of the semipermeable membrane is adapted to cooperate with the osmotic salt to control the release profile of amantadine salt from the osmotic device;

d) the amantadine salt and osmotic salt have an ion in common;

e) amantadine salt is released through the one or more passageways according to a sigmoidal controlled release profile, optionally wherein release of amantadine salt is delayed for a period of time, when the osmotic device is exposed to an aqueous environment of use;

f) the semipermeable membrane comprises a cellulose acetate grade 1 and a cellulose acetate grade 2, wherein the weight ratio of a cellulose acetate grade 1 to the total amount of cellulose acetates ranges from 0:1 to 1:1, wherein the cellulose acetate grade 1 comprises 7-10% by wt. of hydroxyl groups, 30-36% by wt. of acetyl groups and a viscosity of 200-280 seconds, and cellulose acetate grade 2 comprises 3-5% by weight of hydroxyl groups, 37-43% by wt. of acetyl groups and a viscosity of 6.0-45.0 seconds; and g) the osmotic device further comprises a drug-containing coat comprising an active ingredient, wherein the coat is external to the semipermeable membrane.

Yet another aspect of the invention provides an osmotic device comprising a unitary core surrounded by a semipermeable membrane having at least one passageway there through, wherein:

a) the unitary core comprises a mixture of amantadine salt, osmotic salt, and at least one other pharmaceutically acceptable excipient;

b) the amantadine salt and osmotic salt have an ion in common;

c) the weight ratio of amantadine salt to osmotic salt is in the range of 2:1 to 30:1;

d) the semipermeable membrane comprises 1.7%-15.0% by wt. of a plasticizer, 33.3%-61.2% by wt. of cellulose acetate grade 1, and 33.3%-61.2% by wt. of cellulose acetate grade 2, wherein the cellulose acetate grade 1 comprises 7-10% by wt. of hydroxyl groups, 30-36% by wt. of acetyl groups and has a viscosity of 200-280 seconds, and the cellulose acetate grade 2 comprises 3-5% by weight of hydroxyl groups, 37-43% by wt. of acetyl groups and has a viscosity of 6.0-45.0 seconds;

e) amantadine salt is released through the one or more passageways according to a sigmoidal release profile when the osmotic device is exposed to an aqueous environment of use; and f) the osmotic device further comprises a drug-containing coat comprising an active ingredient, wherein the coat is exterior to or on the exterior of the semipermeable membrane.

Some embodiments of the invention include those wherein: 1) the amantadine salt is amantadine hydrochloride, an inorganic salt, or a mineral acid salt.

In some embodiments of the invention include, the osmotic salt is a metal halide, an alkali metal halide, or sodium chloride. The ion in common can be a chloride ion, for example, among other ions.

In some embodiments, the weight ratio of amantadine salt to osmotic salt ranges from 3:1 to 70:1, 4:1 to 30:1, 2:1 to 30:1, or from 2:1 to 600:1.

Some embodiments provide different release rates of and/or release profiles for amantadine. For example, the osmotic device can provide a zero order or pseudo-zero order release of amantadine salt for a period of at least 4 hours, at least 8 hours or at least 12 hours; the semipermeable membrane can have a permeability adapted to cooperate with the sodium chloride in the core such that the osmotic device provides a sigmoidal release profile for amantadine; the semipermeable membrane can have a permeability adapted to cooperate with the sodium chloride in the core such that the osmotic device provides a zero order or pseudo-zero order release profile for amantadine; the semipermeable membrane can have a permeability adapted to cooperate with the sodium chloride in the core such that the osmotic device provides a first order release profile for amantadine; the osmotic device provides a sigmoidal release profile of amantadine salt; or combinations thereof.

Different release rates of or release profiles for amantadine can be achieved by a combination of variables. For example, the semipermeable membrane can comprise a cellulose acetate of high viscosity and a cellulose acetate of lower viscosity; the semipermeable membrane comprises a weight ratio of a cellulose acetate, of about 7%-10% by weight of hydroxyl groups and a viscosity of 200-280 seconds, to the total weight of cellulose acetates from 0:1 to 0.2:1, so that the osmotic device provides a zero order or pseudo-zero order release profile of amantadine salt for a period of at least four hours; the semipermeable membrane comprises a weight ratio of a cellulose acetate, of about 7-10% by weight of hydroxyl groups and a viscosity of 200-280 seconds, to the total weight of cellulose acetates from 0.2:1 to 1:1, so that the osmotic device provides a first order release profile of amantadine salt; or the semipermeable membrane comprises a weight molar ratio of a cellulose acetate, of 7%-10% by weight of hydroxyl groups and a viscosity of 200-280 seconds, to the total weight of cellulose acetates from 0:1 to 1:1, so that the osmotic device provides a sigmoidal release profile of amantadine salt. The invention includes embodiments of the semipermeable membrane wherein: a) the amount of cellulose acetate grade 1 is greater than zero; b) the amount of cellulose acetate grade 2 is greater than zero; c) cellulose acetate grade 1 is absent; d) cellulose acetate grade 1 and cellulose acetate grade 2 are both present; d) cellulose acetate grade 1 is present in excess over cellulose acetate grade 1; and/or e) a plasticizer is present.

In some embodiments, the osmotic device comprises an external coat, i.e. a coat external to the semipermeable membrane, comprising a second active agent (active ingredient) for immediate release of the drug. The external coat can be a rapid release coat. The second active ingredient in the external rapid release coat can be selected from the group consisting of an anti-Parkinsonian drug, antidepressant and an anxiolytic agent. An exemplary includes citalopram. An exemplary anxiolytic agent is buspirone. The active ingredient in the external coat can be amantadine. In some embodiments, the active ingredient in the drug-containing coat is selected from the group consisting of an antidepressant, anxiolytic agent, anti-Parkinson drug, dopamine agonist, COMT (catechol-O-methyl transferase) inhibitor, MAO-B (monoamine oxidase B) inhibitor, anticholinergic, benzodiazepine, SSRI (selective serotonin reuptake inhibitor), nonsteroidal anti-inflammatory agent, non-narcotic analgesic, narcotic analgesic and A2A (adenosine A2A receptor) antagonist. The anti-Parkinson drug in the coat can be selected from the group consisting of amantadine, selegiline, rasagiline, safinamide, diplagurant and tozadenant, or it can be any drug known for the treatment of Parkinson's disease or Parkinsonism. The narcotic analgesic can be selected from the group consisting of codeine, dihydrocodeine, hydrocodone, hydromorphone, levorphanol, morphine, oxycodone and tapentadol or it can be any drug known for the treatment of pain or inflammation.

Alternatively or additionally, some embodiments of the osmotic device further comprise a second active ingredient in the core. The second active ingredient in the core can be a different anti-Parkinsonian drug, i.e. an anti-Parkinsonian drug other than amantadine. In this case, the core will comprise at least amantadine and the different second anti-Parkinsonian drug. The second anti-Parkinsonian drug in the core can be ropinirole, selegiline, levodopa, carbidopa, a combination of levodopa and carbidopa, or a combination thereof.

Some embodiments of the invention includes those wherein the amantadine is released from the core in a controlled manner according to a sigmoidal release profile selected from:

| Time (hours) | Amount Released |
|---|---|
| 0-3 | Not less than 5% |
| 0-5 | Not less than 18% |
| 0-8 | Not less than 39% |
| 0-16 | Not less than 76%; |

| Time (hrs) | Performance Minimum (%) | Performance Maximum (%) |
|---|---|---|
| 0.5 | 0 | 50 |
| 1 | 25 | 55 |
| 2.5 | 45 | 75 |
| 4 | 65 | 95 |
| 8 | 85 | 100; |

| Time (hrs) | Performance Minimum (%) | Performance Maximum (%) |
|---|---|---|
| 0.5 | 0 | 40 |
| 1 | 10 | 40 |
| 2.5 | 30 | 60 |
| 4 | 55 | 85 |
| 8 | 80 | 100; | or

| Time (hrs) | Performance Minimum (%) | Performance Maximum (%) |
|---|---|---|
| 0.5 | 0 | 35 |
| 1 | 15 | 45 |
| 2.5 | 45 | 75 |
| 4 | 65 | 95 |
| 8 | 85 | 100. |

In some embodiments, the core of the osmotic device comprises from about 50 mg to about 75 mg of amantadine, about 75 to about 100 mg of amantadine, or about 100 mg to about 300 mg of amantadine.

In some embodiments, the osmotic device comprises amantadine in the core and amantadine in the external coat, and the total amount of amantadine in the osmotic device range from 65-320 mg. Accordingly, the amount of amantadine in the core will generally range from 50-85% of the total amount present in the osmotic device.

In some embodiments, the osmotic device comprises amantadine in the core and amantadine in the external coat and the dose of amantadine ranges from about 80 mg to about 200 mg for the treatment of fatigue of any kind, i.e. regardless of the etiology of the fatigue.

A sigmoidal release profile can be achieved by balancing result effective variables such as: the ratio of amantadine salt to osmotic salt in the core, the amount or concentration of osmotic salt in the core, the ratio of cellulose acetate grade 1 to the total amount of cellulose acetate in the semipermeable membrane, and/or the amount or concentration of cellulose acetate grade 1 in the semipermeable membrane. In some embodiments when the weight ratio of amantadine salt to osmotic salt ranges from 2:1 to 30:1 or from 4:1 to 30:1, the osmotic device provides a sigmoidal release profile when: a) the amount of osmotic salt in the core is <6% wt., the amount of cellulose acetate grade 1 in the semipermeable membrane is >25%, the ratio of cellulose acetate grade 1 to total amount of cellulose acetate in the semipermeable membrane is >0.25:1 or is 0.3:1 to 0.7:1; b) the amount of osmotic salt in the core is >/=6% wt., the amount of cellulose acetate grade 1 in the semipermeable membrane is <1=25%, the ratio of cellulose acetate grade 1 to total amount of cellulose acetate in the semipermeable membrane is <0.25:1; and c) the amount of osmotic salt in the core is >/=6% wt., the amount of cellulose acetate grade 1 in the semipermeable membrane is >/=25%, the ratio of cellulose acetate grade 1 to total amount of cellulose acetate in the semipermeable membrane is 0.25:1 to 0.4:1 or is 0.25:1 to 0.45:1.

Combinations of the various embodiments disclosed herein are considered within the scope of the invention.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
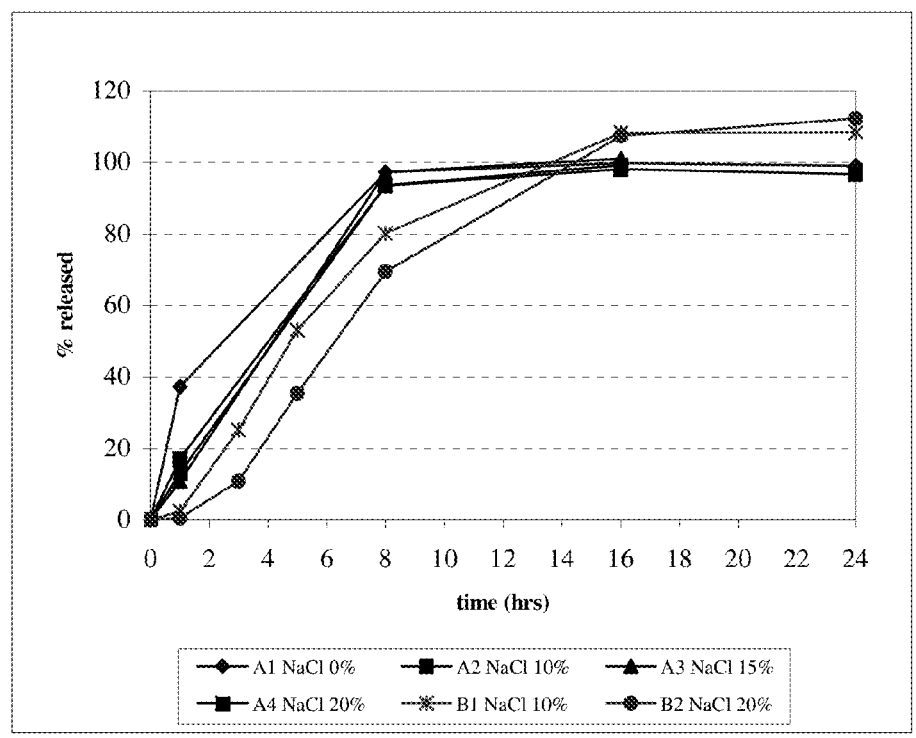
FIG. 1 depicts the in vitro release profiles of amantadine released from the exemplary formulations of Example 1.

The invention provides an osmotic device comprising a unitary core enclosed with a semipermeable membrane having at least one preformed passageway there through. The unitary core comprises a mixture of amantadine salt, osmotic salt and one or more pharmaceutical excipients. The ratio of amantadine salt to osmotic salt is such that the device provides a sigmoidal release of drug. The semipermeable membrane comprises at least two different grades of cellulose acetate. Grade 1 cellulose acetate has a higher viscosity, a higher percentage of hydroxy groups, and a lower percentage of acetyl groups than does grade 2, meaning that grade 2 has a lower viscosity, lower percentage of hydroxyl groups and higher percentage of acetyl groups than does grade 1. The composition of the core, in terms of the amantadine salt to osmotic salt ratio, and the composition of the semipermeable membrane, in terms of the ratio of cellulose acetate grade 1 to the total amount of cellulose acetates present, cooperate together to control the release of amantadine, which is released according to a sigmoidal release profile.

The invention may be better understood by reference to the following definitions provided herein.

By "immediate release" is meant a release of an active agent to an environment over a period of seconds to no more than about 30 minutes once release has begun and release begins within a second to no more than about 15 minutes after administration.

By "rapid release" is meant a release of an active agent to an environment over a period of 1-59 minutes or 1 minute to three hours once release has begun and release can begin within a few minutes after administration or after expiration of a delay period (lag time) after administration.

By "controlled release" is meant a release of an active agent to an environment over a period of about eight hours up to about 12 hours, 16 hours, 18 hours, 20 hours, a day, or more than a day. A controlled release can begin within a few minutes after administration or after expiration of a delay period (lag time) after administration.

By "sustained release" is meant a controlled release of an active agent to maintain a constant drug level in the blood or target tissue of a subject to which the device is administered.

By "extended release" is meant a controlled release of an active agent from a dosage form to an environment over an extended period of time. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "controlled release", "prolonged release", "sustained release", or "slow release", as these terms are used in the pharmaceutical sciences.

A delayed but controlled release dosage form is one that provides a delayed release of a drug followed by a controlled release of the drug. By delayed release is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, or 30 minutes to 10 hours, or 1 hour to 10 hours.

A zero-order release profile characterizes the release profile of a dosage form that releases a constant amount of drug per unit time. A pseudo-zero order release profile is one that approximates a zero-order release profile. A dissolution curve shows a zero or pseudo-zero order release profile if its release rate remains constant (or relatively constant within ±10% of the average value) in the interval of time $0 \leq a < t \leq b$. Any profile following the equation:

$$(M(t)/M_r) = k(t-a)^n \quad 0.9 \leq n \leq 1.1$$

has the following release rate equation:

$$(1/M)(dM/dt) = kn(t-a)^{n-1}$$

Figure 4:
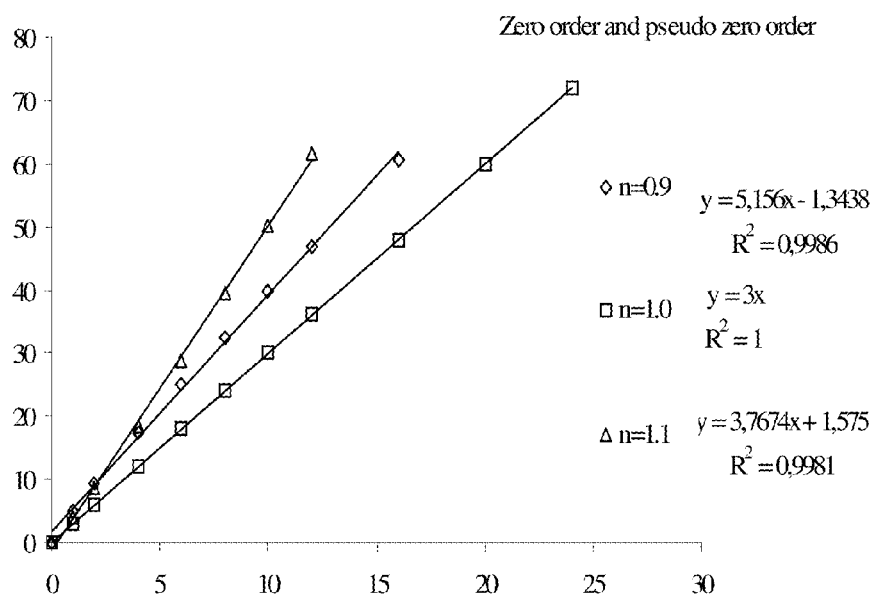
FIGS. 4-6 depict other exemplary in vitro release profiles for release of amantadine.

Exemplary zero or pseudo-zero order release profiles are in FIG. 4.

A sigmoidal release profile characterizes the release profile of a dosage form that releases a drug in a controlled manner but very slowly during a first release period, then more rapidly during a second release period and finally very slowly during a third release period such that the release profile resembles a sigmoid. A dissolution curve shows a sigmoid release profile within a certain interval of time $0 \leq a < t \leq b$ if its release rate reaches a single maximum within the interval (a, b) excluding the extremes. That is equivalent to consider a point of time T* so that the release rate is an increasing function of time for $a \leq t < T^*$ and a decreasing function of time, as determined by the following equation:

Weibull Function $$(M(t)/M_T) = W_{inf}\{1 - \exp\{-[(t-t_i)/\beta]^\alpha\}\}$$

Parameter Ranges:
$t_i$: between 0 and 3
$\beta$: between 7 and 12
$\alpha$: $1 < \alpha < 3$
$W_{inf}$: between 0.5 and 1.1

Figure 5:
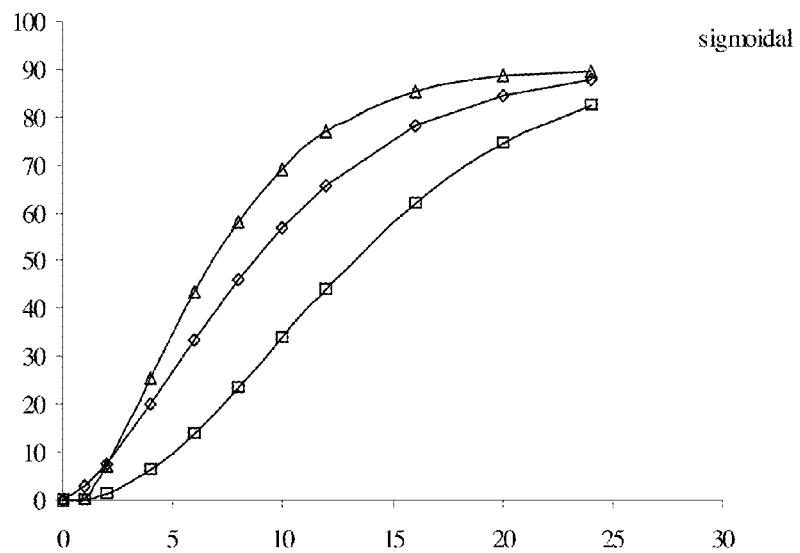

Exemplary sigmoidal release profiles are depicted in FIG. 5.

A first order release profile characterizes the release profile of a dosage form that releases a percentage of a drug charge per unit time. A pseudo-first order release profile is one that approximates a first order release profile. A dissolution curve shows a first or pseudo-first order release profile within a certain interval of time $0 \leq a < t \leq b$ if its release rate is a continue monotone decreasing function of time. Specifically, a dissolution curve shows a first order profile whenever its release rate is proportional to the remaining undissolved amount of drug, as determined by the following equation:

$$(M(t)/MT)=1-\exp(-kt)$$

A dissolution curve shows a pseudo-first order profile when the drug release rate decreases with time as described by the Fickian or anomalous Fickian diffusion controlled release equation:

$$(M(t)/M_T)=kt^n, 0.3 \leq n \leq 0.7$$

Figure 6:
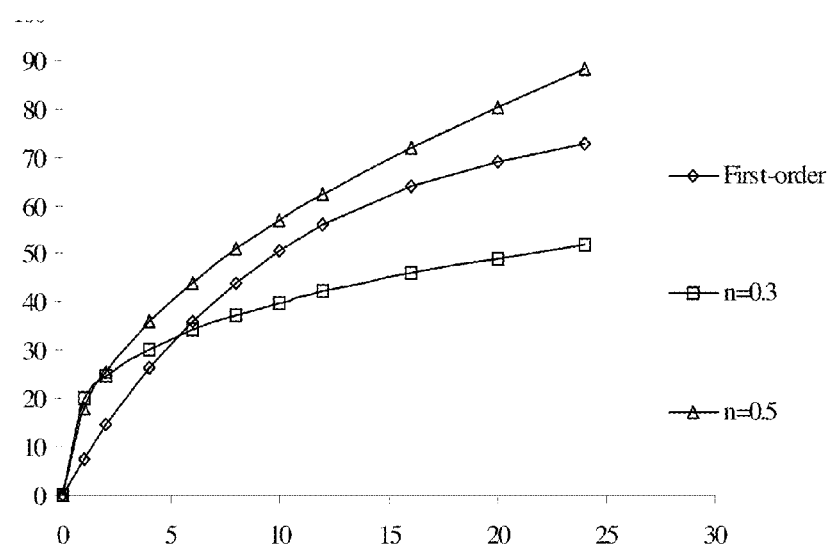

Exemplary first order release profiles are depicted in FIG. 6.

By "unitary core" is meant the core of an osmotic device that is not divided into two or more layers or laminas. The core is considered to be the composition enclosed within the semi-permeable membrane of the osmotic device. The ingredients of the core may be present as a heterogeneous mixture or homogeneous mixture. A homogeneous mixture is one wherein all of the ingredients have been thoroughly mixed such that the composition of the formulation is substantially the same throughout different portions of the core. The combined step of mixing and directly compressing the ingredients of the core generally provides a homogeneous mixture. A heterogeneous mixture is one wherein the ingredients of the core are divided into two or more groups that are processed separately to form two or more respective blends, at least one of which contains drug and at least one of which contains the osmotic salt. The blends are then mixed together and compressed to form the unitary core. A heterogeneous mixture can be obtained by wet granulation, dry granulation, pelleting or combinations thereof.

Amantadine hydrochloride is available commercially from companies such as Northeast General Pharmaceutical Factory (Shenyang, China). When used herein, the term amantadine refers to the free-base or salt form of amantadine. Amantadine salt can be present as an inorganic acid addition salt. The inorganic salt of amantadine is generally a mineral acid salt. The hydrochloride, hydrobromide, hydroiodide, nitrate, sulfate, bisulfate, or phosphate salts are useful. The hydrochloride salt of amantadine is particularly suitable for use according to the invention.

The osmotic salt is an organic or inorganic salt, wherein the osmotic salt and the amantadine salt have an ion in common. By "ion in common" is meant that amantadine salt and the osmotic salt each have ions of the same identity. It is not meant that amantadine salt and the osmotic salt actually share the same ion. The inorganic osmotic salt is typically a metal halide, in particular an alkali metal halide or an earth metal halide, or more particularly sodium chloride. By way of example and without limitation, amantadine hydrochloride and NaCl have the chloride ion in common.

The release profiles of the osmotic device tablets of the invention will vary according to the amount of sodium chloride present in the core.

FIG. 1 depicts amantadine in vitro dissolution profiles for the osmotic device tablets described in Example 1. The in vitro testing was performed with USP Type II dissolution apparatus (paddles), in 900 ml distilled water with a fixed agitation rate of 50 revolutions per minute, maintained at a temperature of 37±0.5° C. The samples were tested by gas chromatography.

The release profiles obtained for six tablets (#1-#6) of the osmotic device tablets containing 0% of sodium chloride in the core coated with coating formulation A (FIG. 1, A1 NaCl 0%) are disclosed in the table below, which detail the amount of amantadine released at the indicated time points, based upon when the osmotic device was exposed to the release liquid medium. The release profile approximates a first order release profile.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 39.6 | 37.9 | 35.7 | 35.5 | 39.2 | 35.6 |
| 8 | 95.3 | 98.9 | 96.8 | 97.4 | 98.3 | 96.5 |
| 16 | 98.9 | 97.2 | 100.5 | 102.5 | 97.3 | 102.3 |
| 24 | 97.7 | 98.1 | 99.4 | 100.4 | 97.3 | 101.9 |

| Time (hrs) | Average (%) | SD (%) | Max (%) | Min (%) |
|---|---|---|---|---|
| 1 | 37.3 | 1.9 | 40 | 36 |
| 8 | 97.2 | 1.3 | 99 | 95 |
| 16 | 99.8 | 2.4 | 103 | 97 |
| 24 | 99.1 | 1.8 | 102 | 97 |

The release profiles obtained for six tablets (#1-#6) of the osmotic device tablets containing 10% of sodium chloride in the core coated with coating formulation A (FIG. 1, A2 NaCl 10%) are disclosed in the table below, which detail the amount of amantadine released at the indicated time points, based upon when the osmotic device was exposed to the release liquid medium. The release profile approximates a zero order or pseudo-zero order release profile.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 19.7 | 22.7 | 10.4 | 15.6 | 11.3 | 23.1 |
| 8 | 92.6 | 94.0 | 91.8 | 95.3 | 92.2 | 95.1 |
| 16 | 97.2 | 98.4 | 97.9 | 99.2 | 98.7 | 97.5 |
| 24 | 95.6 | 96.9 | 97.0 | 97.4 | 95.9 | 97.1 |

| Time (hrs) | Average (%) | SD (%) | Max (%) | Min (%) |
|---|---|---|---|---|
| 1 | 17.1 | 5.6 | 23 | 10 |
| 8 | 93.5 | 1.5 | 95 | 92 |
| 16 | 98.2 | 0.8 | 99 | 97 |
| 24 | 96.7 | 0.7 | 97 | 96 |

The release profiles obtained for six tablets (#1-#6) of the osmotic device tablets containing 15% of sodium chloride in the core coated with coating formulation A (FIG. 1, A3 NaCl 15%) are disclosed in the table below, which detail the amount of amantadine released at the indicated time points, based upon when the osmotic device was exposed to the release liquid medium. The release profile approximates a zero order release profile.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 9.8 | 16.9 | 4.6 | 11.5 | 6.3 | 15.8 |
| 8 | 93.4 | 98.3 | 95.8 | 101.1 | 93.9 | 100.8 |
| 16 | 102.4 | 104.4 | 100.5 | 96.7 | 103.2 | 98.8 |

| Time (hrs) | Average (%) | SD (%) | Max (%) | Min (%) |
|---|---|---|---|---|
| 1 | 10.8 | 4.9 | 17 | 5 |
| 8 | 97.2 | 3.4 | 101 | 93 |
| 16 | 101.0 | 2.9 | 104 | 97 |

The release profiles obtained for six tablets (#1-#6) of the osmotic device tablets containing 20% of sodium chloride in the core coated with coating formulation A (FIG. 1, A4 NaCl 20%) are disclosed in the table below, which detail the amount of amantadine released at the indicated time points, based upon when the osmotic device was exposed to the release liquid medium. The release profile approximates a zero order release profile.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 13.1 | 10.1 | 15.2 | 15.5 | 10.5 | 14.9 |
| 8 | 94.6 | 93.8 | 91.3 | 95.4 | 91.7 | 95.3 |
| 16 | 99.4 | 102.2 | 99.1 | 95.8 | 102.4 | 96.3 |

| Time (hrs) | Average (%) | SD (%) | Max (%) | Min (%) |
|---|---|---|---|---|
| 1 | 13.2 | 2.4 | 16 | 10 |
| 8 | 93.7 | 1.8 | 95 | 91 |
| 16 | 99.2 | 2.8 | 102 | 96 |

The release profiles obtained for six tablets (#1-#6) of the osmotic device tablets containing 10% of sodium chloride in the core coated with coating formulation B (FIG. 1, B1 NaCl 10%) are disclosed in the table below, which detail the amount of amantadine released at the indicated time points, based upon when the osmotic device was exposed to the release liquid medium. The release profile is sigmoidal in shape have a first slow-release phase, a following faster release phase, and a final slow-release phase.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 3.3 | 2.9 | 2.2 | 1.7 | 3.0 | 1.9 |
| 3 | 21.6 | 30.1 | 24.9 | 23.7 | 21.8 | 29.8 |
| 5 | 49.2 | 57.1 | 56.8 | 51.2 | 56.7 | 48.1 |
| 8 | 79.5 | 81.6 | 86.1 | 73.8 | 85.9 | 74.7 |
| 16 | 106.2 | 106.2 | 115.7 | 103.9 | 113.3 | 104.1 |
| 24 | 107.7 | 105.9 | 115.5 | 106.0 | 110.4 | 104.9 |

| Time (hrs) | Average (%) | SD (%) | Max (%) | Min (%) |
|---|---|---|---|---|
| 1 | 2.5 | 0.7 | 3 | 2 |
| 3 | 25.3 | 3.8 | 30 | 22 |
| 5 | 53.2 | 4.2 | 57 | 48 |
| 8 | 80.3 | 5.3 | 86 | 74 |
| 16 | 108.2 | 5.0 | 116 | 104 |
| 24 | 108.4 | 4.0 | 116 | 105 |

The release profiles obtained for six tablets (#1-#6) of the osmotic device tablets containing 20% of sodium chloride in the core coated with coating formulation B (FIG. 1, B2 NaCl 20%) are disclosed in the table below, which detail the amount of amantadine released at the indicated time points, based upon when the osmotic device was exposed to the release liquid medium. The release profile approximates that of B1 except that it has a slower initial release of drug that causes a delay in the second phase of drug release.

| Time (hrs) | Rel. (%) #1 | Rel. (%) #2 | Rel. (%) #3 | Rel. (%) #4 | Rel. (%) #5 | Rel. (%) #6 |
|---|---|---|---|---|---|---|
| 1 | 2.5 | 0 | 0 | 0 | 0 | 1.2 |
| 3 | 14.9 | 6.2 | 11.7 | 10.5 | 14.6 | 7.1 |
| 5 | 44.2 | 21.2 | 39 | 37.6 | 43.9 | 27.1 |
| 8 | 75.3 | 60.9 | 71.8 | 70.1 | 74.7 | 63.8 |
| 16 | 106.4 | 105.8 | 107.3 | 110.2 | 109.9 | 104.7 |
| 24 | 108.7 | 115.4 | 110.7 | 114.0 | 113.6 | 111.2 |

| Time (hrs) | Average (%) | SD (%) | Max (%) | Min (%) |
|---|---|---|---|---|
| 1 | 0.6 | 1.0 | 2.5 | 0.0 |
| 3 | 10.8 | 3.7 | 14.9 | 6.2 |
| 5 | 35.5 | 9.4 | 44.2 | 21.2 |
| 8 | 69.4 | 5.9 | 75.3 | 60.9 |
| 16 | 107.4 | 2.2 | 110.2 | 104.7 |
| 24 | 112.3 | 2.5 | 115.4 | 108.7 |

Increasing the amount of sodium chloride in the core coated with coating formulation A of the osmotic device tablets of Example 1 reduces the rate of release of amantadine, and modifies the release profile of amantadine from a first order release profile to a zero order release profile as shown in FIG. 1 (release profiles A1 NaCl 0%, A2 NaCl 10%, A3 NaCl 15%, and A4 NaCl 20%). Increasing the amount of sodium chloride in the core coated with coating formulation B of Example 1 reduces the rate of release of amantadine and modifies the release profile of amantadine by extending the delay of the beginning of the controlled release of the amantadine as shown in FIG. 1 (release profiles B1 NaCl 10%, and B2 NaCl 20%).

The permeability of the semipermeable membrane can be adapted to cooperate with the osmotic salt to control the release profile of amantadine salt from the osmotic device. The permeability is different for semipermeable membranes A and B, above. The composition of semipermeable membrane B is such that the cooperation between semipermeable membrane B and the osmotic salt provides initially very slow controlled release of drug for a first release period of about one to three hours, followed by a more rapid controlled release of drug for a second release period of about four to five hours, and finally another slow controlled release of drug for a third period of eight to sixteen hours. In other words, membrane B affects a sigmoidal release of drug. The composition of semipermeable membrane A is such that the cooperation between semipermeable membrane A and the osmotic salt provides a zero order release or pseudo-zero order release of drug for a period of about eight to ten hours such that substantially all of the drug is released within about ten hours.

The composition of the semipermeable membrane can be adapted to provide membranes differing in permeability. The exemplary formulation of membrane A (Example 1) comprises about 85.7% to 98.3% of a cellulose ester grade 1, and about 1.7% to 15.0% of a plasticizer.

The exemplary formulation of membrane B (Example 1) comprises about 33.3%-61.2% of a first cellulose ester grade 1, about 33.3%-61.2% of a second cellulose ester grade 2, and about 1.7%-15.0% of a plasticizer, expressed as percentage of the weight of the membrane coating.

Figure 2:
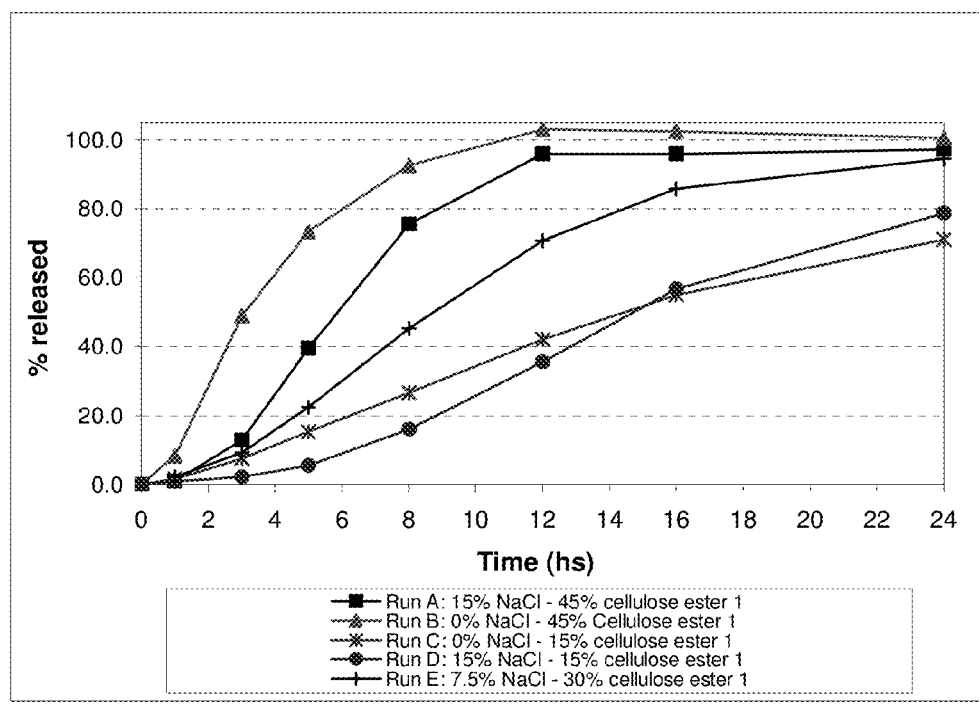
FIGS. 2 and 3 depict the in vitro release profiles of amantadine released from the exemplary formulations of Example 2.
Figure 3:
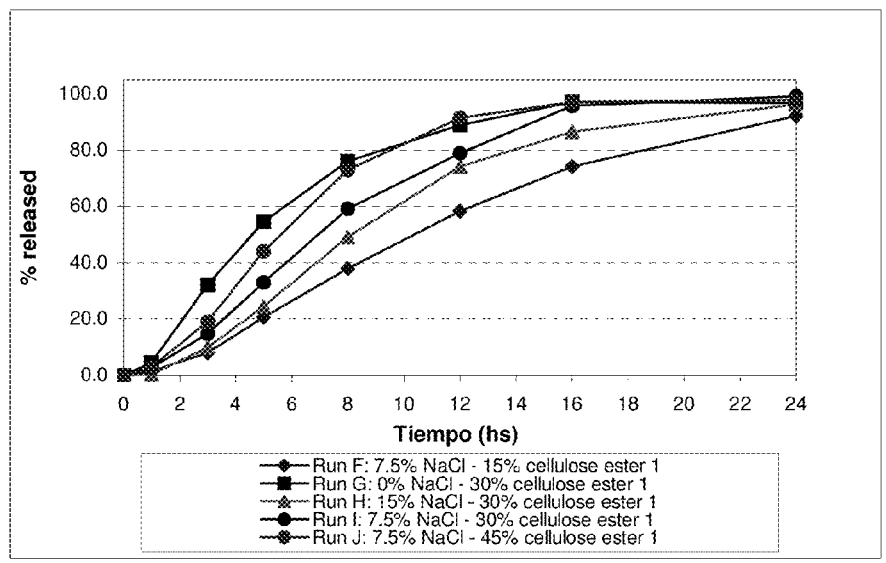
Figure 7:
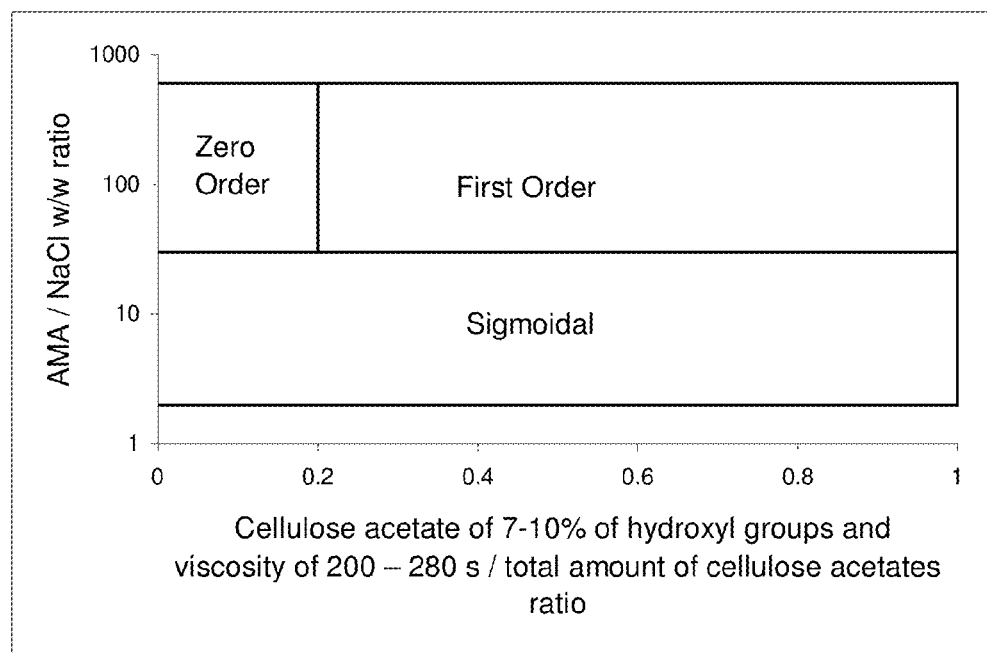
FIG. 7 depicts the regions corresponding to the first, zero, and sigmoidal release profiles according to the limits of amantadine HCl/NaCl (weight/weight) ratio and the cellulose acetate of 7-10% of hydroxyl groups and viscosity of 200-280 seconds to the total amount of cellulose acetates (weight/weight) ratio of formulations of Example 2.

The amantadine HCl osmotic device tablets of 300 mg strengths (Example 2) manufactured comprising varying amounts of sodium chloride in the core, and varying amounts of two different cellulose acetate polymers in the semipermeable membrane, provide a corresponding different amantadine release profiles including first order release profiles, zero order release profiles, and sigmoidal release profiles (FIGS. 2 and 3, release profiles runs A through J). Dissolution curves A to J were related to composition parameters by using a nonlinear mixed effect model from which three regions (FIG. 7) corresponding respectively to zero or pseudo-zero order, first or pseudo-first order and sigmoidal profiles were defined. The weight ratios of amantadine HCl/NaCl in the core and of the cellulose acetate polymer grade 1 to total cellulose acetate polymer present in the semipermeable membrane define the three regions of characteristic dissolution curve shapes. The composition parameters limits that define those regions are shown in following table.

| Combination | Profile Regions or types | Amantadine HCl/NaCl (w/w) | | Cellulose acetates Ratio (w/w) | |
|---|---|---|---|---|---|
| I | First order | 600/1 | 30/1 | 0.2/1 | 1/1 |
| II | Zero order | 600/1 | 30/1 | 0/1 | 0.2/1 |
| II | Sigmoid | 30/1 | 2/1 | 0/1 | 1/1 |

The weight ratio of cellulose acetates in the semipermeable membrane is defined as the ratio of the weight of cellulose acetate grade 1 to the total weight of cellulose acetate polymer(s) present in the semipermeable membrane, wherein the semipermeable membrane comprises a defined amount of cellulose acetate grade 1, a plasticizer and a defined amount of cellulose acetate grade 2. Therefore, a cellulose acetate weight ratio of 0.2:1 defines a semipermeable membrane comprising 20% by weight of cellulose acetate grade 1 and 80% by wt. of cellulose acetate grade 2 based upon the total weight of cellulose acetates present in the semipermeable membrane. A cellulose acetate weight ratio of 0:1 defines a semipermeable membrane comprising cellulose acetate grade 2 and plasticizer but no cellulose acetate grade 1, meaning that cellulose acetate grade 1 is excluded from the membrane or meaning that 100% by wt. of the cellulose acetate in the membrane is of the grade 2. A cellulose acetate weight ratio of 1:1 defines a semipermeable membrane comprising 100% by weight of cellulose acetate grade 1 based upon the total weight of cellulose acetates present in the membrane, whereby the membrane comprises cellulose acetate grade 1 and plasticizer and excludes cellulose acetate grade 2. It should be noted that the weight of plasticizer is not included in the calculation for determination of weight ratio of cellulose acetate. Even though the above text refers to cellulose acetate grades 1 and 2, it is possible for cellulose acetate grade 3 (see below) to be used in place of cellulose acetate grade 1 or grade 2. Likewise, it is also possible for the semipermeable membrane to comprise the three different grades of cellulose acetate in addition to a plasticizer.

When osmotic devices having the Combination I weight ratios are prepared, they provide a first order or pseudo-first order release of amantadine for a period of at least four hours, at least 8 hours or at least 12 hours. A Combination I osmotic device comprises an amantadine HCl to NaCl weight ratio ranging from 600:1 to 30:1 and a cellulose acetate weight ratio ranging from 0.2:1 to 1:1. Thus, the weight percentage of cellulose acetate grade 1 can range from 20% to 100% by wt. and the weight percentage of cellulose acetate grade 2 can range from 80% to 0% by wt., respectively, based upon the total amount of cellulose acetate present in the semipermeable membrane, i.e. not based upon the total weight of the semipermeable membrane itself which may include other components as described herein.

When osmotic devices having the Combination II weight ratios are prepared, they provide a zero order or pseudo-zero order release profile of amantadine salt for a period of at least four hours, at least 8 hours or at least 12 hours. A Combination II osmotic device comprises an amantadine HCl to NaCl weight ratio ranging from 600:1 to 30:1 and a cellulose acetate weight ratio ranging from 0:1 to 0.2:1. Thus, the weight percentage of cellulose acetate grade 1 can range from 0% to 20% by wt. and the weight percentage of cellulose acetate grade 2 can range from 100% to 80% by wt., respectively, based upon the total amount of cellulose acetate present in the semipermeable membrane.

When osmotic devices having the Combination III weight ratios are prepared, they provide a sigmoidal release profile of amantadine salt A Combination III osmotic device comprises an amantadine HCl to NaCl weight ratio ranging from 30:1 to 2:1 and a cellulose acetate weight ratio ranging from 0:1 to 1:1. Thus, the weight percentage of cellulose acetate grade 1 can range from 0% to 100% by wt. and the weight percentage of cellulose acetate grade 1 can range from 100% to 0% by wt., respectively, based upon the total amount of cellulose acetate present in the semipermeable membrane.

According to some embodiments, the osmotic device has a weight ratio of amantadine salt to osmotic salt ranging from 4:1 to 30:1, the semipermeable membrane comprises a weight ratio of a cellulose acetate grade 1 to the total amount of cellulose acetates of from 0.3:1 to 0.7:1, and the osmotic device provides a sigmoidal release profile of amantadine salt.

The dosage forms prepared according to certain embodiments of the present invention preferably exhibit the following dissolution profile when tested in a USP Type II dissolution apparatus (paddles), in 900 ml distilled water with a fixed agitation rate of 50 revolutions per minute, maintained at a temperature of 37±0.5° C.

| Time (hours) | Preferred | Most preferred |
|---|---|---|
| 0-3 | Not less than 5% | Not less than 16% |
| 0-5 | Not less than 18% | Not less than 35% |
| 0-8 | Not less than 39% | Not less than 55% |
| 0-16 | Not less than 76% | Not less than 84% |

In some embodiments, wherein the unitary core comprises less than 6% of NaCl w/w based upon the weight of the uncoated core, and the semipermeable membrane comprises more than 25% w/w of cellulose acetate grade 1 based upon the weight of the semipermeable membrane, the amantadine is released from the core according to the following sigmoidal release profile:

| Time (hrs) | Performance Minimum (%) | Performance Maximum (%) |
| --- | --- | --- |
| 1 | 0 | 4 |
| 3 | 16 | 27 |
| 5 | 35 | 59 |
| 8 | 55 | 83 |
| 12 | 77 | 100 |
| 16 | 84 | 100 |
| 24 | 86 | 100. |

In some embodiments, wherein the unitary core comprises more than 6% of NaCl w/w, based upon the weight of the uncoated core, and the semipermeable membrane comprises more than 25% w/w of cellulose acetate grade 1, based upon the weight of the semipermeable membrane, the amantadine is released from the core according to the following sigmoidal release profile.

| Time (hrs) | Performance Minimum (%) | Performance Maximum (%) |
| --- | --- | --- |
| 1 | 0 | 4 |
| 3 | 5 | 20 |
| 5 | 18 | 43 |
| 8 | 39 | 73 |
| 12 | 62 | 99 |
| 16 | 76 | 100 |
| 24 | 84 | 100. |

In some embodiments, wherein the unitary core comprises more than 6% of NaCl w/w, based upon the weight of the uncoated core, and the semipermeable membrane comprises less than 25% w/w of cellulose acetate grade 1, based upon the weight of the semipermeable membrane, the amantadine is released from the core according to the following sigmoidal release profile:

| Time (hrs) | Performance Minimum (%) | Performance Maximum (%) |
| --- | --- | --- |
| 1 | 0 | 2 |
| 3 | 0 | 6 |
| 5 | 5 | 21 |
| 8 | 15 | 55 |
| 12 | 29 | 84 |
| 16 | 42 | 100 |
| 24 | 62 | 100. |

In some embodiments, wherein the unitary core comprises more than 6% of NaCl w/w, based upon the weight of the uncoated core, and the semipermeable membrane comprises more than 25% w/w of cellulose acetate grade 1, based upon the weight of the semipermeable membrane, the amantadine is released from the core according to a sigmoidal release profile. For example, Run A in FIG. 2 represents the release profile of an osmotic device containing 15% NaCl and 45% cellulose ester 1. It is important to note that this osmotic device has an overall ratio of cellulose acetate grade 1 to total amount of cellulose acetate of 0.25:1 to 0.4:1 for the semipermeable membrane.

The osmotic device of the invention can comprise a water soluble and/or erodible coating, which is inert or which contains drug. This coating would cover and surround the semipermeable membrane and plug any preformed passageway in the membrane if the passageway had been formed prior to addition of the coating. The water soluble and/or erodible coating will generally comprise an inert and non-toxic material that is at least partially, and optionally substantially completely, soluble or erodible in an environment of use. Selection of materials suitable for the inert or drug-containing water soluble coatings will depend upon the desired release rate of drug from the drug-containing coating and upon the desired separation of drug delivery from the core versus the drug-containing coating. A rapidly dissolving coat will be soluble in the buccal cavity and/or upper GI tract, such as the stomach, duodenum, jejunum or upper small intestines. Exemplary materials are disclosed in U.S. Pat. Nos. 4,576,604 to Guittard et al. and 4,673,405 to Guittard et al., and 6,004,582 to Faour et al. and the text *Pharmaceutical Dosage Forms: Tablets Volume I, 2$^{nd}$ Edition.* (A. Lieberman. ed. 1989, Marcel Dekker, Inc.), the relevant disclosures of which are hereby incorporated by reference. In some embodiments, the rapidly dissolving coat will be soluble in saliva, gastric juices, or acidic fluids.

Materials which are suitable for making the water soluble and/or erodible coatings of the invention include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. The water soluble coating can comprise other pharmaceutical excipients that do or do not alter the way in which the water soluble coating behaves. The artisan of ordinary skill will recognize that the above-noted materials include film-forming polymers.

Other materials which can be used in the water soluble and/or erodible coatings include hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethyl-methacrylate (HEMA), MMA, terpolymers of HEMA:MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the water soluble coat.

The inert water soluble and/or erodible coat covering the semipermeable wall and blocking the passageway is made of synthetic or natural material that, through selective dissolution or erosion, allows the passageway to become unblocked thus allowing the process of osmotic delivery to start. This slow or fast dissolving water soluble coat can be impermeable to a first external fluid, while being soluble in a second external fluid. This property can help to achieve a controlled and selective release of the active compound in the nucleus.

In some embodiments, the inert water soluble and/or erodible coat will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the water soluble coat. Such other polymeric materials include, by way of example and without limitation, cellulose acetate phthalate (CAP), cellulose acetate trimelletate (CAT), poly(vinyl acetate)phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit™ L-30-D (MA-EA, 1:1), Eudragit™ L-100-55 (MA-EA, 1:1), hydroxypropyl methylcellulose acetate succinate (HPMCAS), Coateric™ (PVAP), Aquateric™ (CAP), AQOAT™ (HPMCAS) and combinations thereof. The water-soluble coat can also comprise dissolution aids, stability modifiers, and bioabsorption enhancers.

An optional polymeric material for use in the inert water soluble and/or erodible coat includes enteric materials that resist the action of gastric fluid avoiding permeation through the semipermeable wall while one or more of the materials in the core are solubilized in the intestinal tract thereby allowing delivery of a drug in the core by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The water soluble and/or erodible coat can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon™ K 30 has a viscosity of about 5.5-8.5 cps at 20.degree. C., and a 2% P/V aqueous solution of Methocel™ E-15 has a viscosity of about 13-18 cps at 20.degree. C.

The inert water soluble and/or erodible coat can also comprise other materials suitable which are substantially resistant to gastric juices and which will promote either enteric or colonic release. For this purpose, the inert water soluble and/or erodible coat can comprise one or more materials that do not dissolve, disintegrate, or change their structure in the stomach and during the period of time that the osmotic device resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with acetyl alcohol; (f) acrylic resins represented by anionic polymers synthesized from methacrylic acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials that form a semipermeable wall which are known by those of ordinary skill in the art of pharmaceutical sciences are suitable for this purpose. Exemplary materials are cellulose esters, cellulose ethers and cellulose esters-ethers. However, it has been found that a semipermeable membrane comprising cellulose acetate (CA) and poly(ethylene glycol) (PEG), in particular PEG 400, performs well when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50-99% by weight of CA: about 50-1% by weight of PEG, and about 95% by weight of CA: about 5% by weight of PEG. The ratio can be varied to alter permeability and ultimately the release profile of the osmotic device. Other suitable materials can include a selected member of the group of cellulose acylates such as cellulose acetate, cellulose diacetate, cellulose triacetate and combinations thereof. Many suitable polymers, include those disclosed in Argentine Patent No. 199,301, U.S. Pat. No. 6,004,582 and references cited herein, the disclosures of which are hereby incorporated by reference.

Representative materials include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%; a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. Nos. 3,173,876, 3,276,586, 3,541,005, 3,541,006, and 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride). These and others polymers are disclosed in U.S. Pat. Nos. 3,845,770, 3,916,899, 4,765,989 and 4,160,020; and in *Handbook of Common Polymers* (Scott, J. R. and Roff, W. J., eds.; 1971; CRC Press, Cleveland, Ohio).

The cellulose esters differ in their cellulose chain length and the type and amount of ester groups attached to the chain. For cellulose acetates, as the amount of acetyl content increases, the permeability decreases. The cellulose acetate grade 1 comprises 7-10% by weight of hydroxyl groups and has a viscosity of 200-280 seconds as determined by ASTM Method D 1343. The cellulose acetate grade 2 comprises 3-5% by weight of hydroxyl groups and has a viscosity of 6 to 45 seconds. The cellulose acetate grade 3 comprises 3-5% by weight of hydroxyl groups and has a viscosity of 100 to 240 seconds.

Some exemplary grades of cellulose acetate that are suitable for use in the making the semipermeable membrane are also described in the table below, which is included by way of example. Cellulose acetate of differing grades is readily available from Eastman Chemical Company (Kingsport, Tenn., USA).

| Cellulose Acetate | Hydroxyl Content (% by wt.) | Acetyl Content (% by wt.) | Viscosity* (seconds) |
| --- | --- | --- | --- |
| Grade 1 | 7-10 | 30-36 | 200-280 |
| Grade 2 | 3-5 | 37-43 | 6-45 |
| Grade 3 | 3-5 | 37-43 | 100-240 |

*Viscosity determined as set forth in ASTM D817 (Formula A) and D1343, the disclosure of which is hereby incorporated by reference.

Plasticizers can be included in the present device to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

An alternative embodiment of the invention includes pore former(s) in the wall to form additional passageways over time.

Release of active agent from the core can be delayed such that the release profile of active agent will exhibit delayed and then controlled release. Such a device would be termed a delayed controlled release device.

The osmotic device of the invention comprises at least one passageway (pore, hole, or aperture) that communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. Nos. 4,088,864 to Theeuwes et al., 4,016,880 to Theeuwes et al., 3,916,899 to Theeuwes et al., 4,285,987 to Ayer et al., 4,783,337 to Wong et al., 5,558,879 to Chen et al., 4,801,461 to Hamel et al., 3,845,770 to Theeuwes et al., PCT International Publication No. WO 04/103349 to Faour, and U.S. Pat. No. 6,809,288 to Faour, the disclosures of which are hereby incorporated by reference.

The preformed passageway in the wall is typically generated by mechanical means, such as perforation by a laser or drill, or any other similar method known to those of ordinary skill in the art. The passageway is generally formed by controlled laser perforation, using an apparatus similar to that disclosed in Theeuwes et al. '864, the entire disclosure of which is incorporated herein by reference. Specific embodiments of the controlled laser perforation method will vary according to the equipment used. The laser equipment of Theeuwes et al. '864 can be modified as described herein to prepare an osmotic device according to the invention. Other suitable laser equipment, are methods of use thereof, are disclosed in Emerton et al. '793 and Roy '771, the entire disclosures of which are hereby incorporated by reference. The process and system of Faour (U.S. Pregrant Patent Publication No. 2002/0099361) can also be used to form the preformed passageway and/or etch in the wall.

A preformed passageway can be made to substantially retain its size during use of the device or it can be made to increase in size during use of the dosage form. Preformed passageways of different sizes, shapes and functions can be used.

The preformed passageway in the wall may dissolve or tear in a predetermined or random manner, and the shape of the preformed passageway after enlargement can be made to approximate a predetermined or randomly determined shape. The extent to which a passageway increases in size can also be related to the viscosity, molecular weight or degree of substitution of the at least one excipient. Generally, increasing the viscosity, molecular weight, or degree of substitution of the at least one excipient will increase the extent to which the passageway increases in size.

A device according to the present invention can comprise one or more preformed passageways including two, three, four, five, six, seven, eight, nine, ten or more preformed passageways. It is only necessary that the preformed passageways together are adapted to permit controlled release of ingredients from the core during use. In some embodiments, the membrane comprises one preformed passageway having a diameter ranging from 0.2 mm to 0.8 mm. In other embodiments, the total area of the preformed passageway(s) present in the membrane ranges from 0.12 mm$^2$ to 2.1 mm$^2$.

The core of the osmotic device of the present invention will comprise an active agent and an osmotic agent and can further comprise many other materials as discussed herein. The amount of active agent present can vary as described above for the external coat. Generally, the active agent will be present in an amount ranging from 0.1-99.9% by weight of the uncoated core. Specific ranges will vary according to the active agent used and the intended use of the osmotic device.

The osmotic device of the invention can comprise osmotically effective solutes or osmotic agents, i.e. osmagents, that are capable of being totally or partially solubilized in the fluid. These osmagents will aid in either the suspension or dissolution of amantadine from the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, magnesium succinate, sodium succinate, sodium butyrate, sodium fumarate, sodium benzenesulfonate, sodium toluenesulfonate, sodium methanesulfonate, combinations thereof and other similar or equivalent materials which are widely known in the art. U.S. Pat. No. 4,077,407 to Theeuwes et al., the entire disclosure of which is hereby incorporated by reference, discloses suitable osmagents.

One or more osmopolymers can also be added to the core of the device to aid in the delivery of active agents. Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, sodium carboxymethylcellulose, hydroxypropyl methylcellulose, polyethylene oxide, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides. These materials swell or expand to an equilibrium state when exposed to water or other biological fluids. This volume expansion is used to physically force the pharmaceutical agent out through openings that have been formed in the wall, shell or coating during manufacture. A water insoluble active agent is primarily released as insoluble particles, which therefore have limited bioavailability. Exemplary osmopolymers are disclosed in U.S. Pat. Nos. 5,422,123; 4,783,337; 4,765,989; 4,612,008; 4,327,725; 4,609,374; 4,036,228; 4,992,278; 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in one embodiment, lightly cross-linked, such as cross-links being formed by covalent or ionic bonds.

The osmotic device of the invention can also comprise an adsorbent, antioxidant, buffering agent, colorant, flavorant, sweetening agent, antiadherent, binder, diluent, direct compression excipient, disintegrant, glidant, lubricant, opaquant and/or polishing agent.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "binder" is intended to mean a substance used to cause adhesion of powder particles in tablet granulations. Such compounds include, by way of example and without limitation, acacia, alginic acid, carboxymethylcellulose sodium, poly(vinylpyrrolidone), compressible sugar (e.g., NuTab™), ethylcellulose, gelatin, liquid glucose, methylcellulose, povidone and pregelatinized starch and other materials known to one of ordinary skill in the art.

When needed, a binder may also be included in the present device. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and others known to those of ordinary skill. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "diluent" or "filler" is intended to mean an inert substance used as filler to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "polishing agent" is intended to mean a compound used to impart an attractive sheen to coated tablets. Such compounds include, by way of example and without limitation, carnauba wax, and white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and *cassia* oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present device can also employ one or more commonly known surface active agents or cosolvents that improve wetting or disintegration of the osmotic device core or layers.

It is contemplated that the osmotic device of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly (oxypropylene) copolymers; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of therapeutic compound incorporated in each device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient.

The term "unit dosage form" is used herein to mean a device containing a quantity of the therapeutic compound, said quantity being such that one or more predetermined units may be provided as a single therapeutic administration.

The device of the invention can be prepared according to the methods disclosed herein or those well known in the art. For example, according to one manufacturing technique, the active agent and excipients that comprise the core can be mixed in solid, semisolid or gelatinous form, then moistened and sieved through a specified screen to obtain a granulate. The granulate is then dried in a dryer and compressed, for example, by punching to form uncoated cores. The compressed and uncoated cores are then covered with a solution of suitable materials that comprise the wall. Subsequently, the wall surrounding each core is perforated with, for example, laser equipment to form the preformed passageway in the manner previously described. When needed a drug-containing external coat can be applied to cover the wall as a sprayed coating or a compression coating. If desired, the device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The dosage form of the invention is used in various methods of treating diseases, disorders and/or symptoms that are therapeutically or clinically responsive to amantadine therapy. Symptoms, disorders and/or diseases that are responsive to amantadine therapy include, but are not limited to, Parkinson's disease, drug-induced extrapyramidal reactions, viral infection, and signs and symptoms of infection caused by various strains of influenza A virus, especially for high-risk patients such as those in critical public-service positions, immunosuppressed patients, nursing home residents, contacts of high-risk patients, and those with severe influenza A viral infection. The dosage form of the invention is also used in various methods of treating diseases, disorders and/or symptoms that are responsive to a combination of amantadine and a second drug. The invention includes an osmotic device for the combined administration of amantadine in a controlled release manner and an antidepressant in an immediate or rapid release manner, e.g., the combination of amantadine and citalopram (Example 3), or fluoxetine, paroxetine, sertraline, fluvoxamine or escitalopram. The invention also includes an osmotic device for the combined administration of amantadine in a controlled release manner and an anxiolytic agent in an immediate or rapid release manner, e.g., amantadine and buspirone (Example 4) or trazodone, for the amelioration of undesired tremors, akinesia, dyskinesia, or bradykinesia associated with one or more different disorders or diseases. The invention also includes an osmotic device for the combined administration of amantadine and a second anti-Parkinsonian drug in a controlled release manner from the core, e.g., amantadine and ropinirole, or selegiline, or levodopa-carbidopa. The term "anti-Parkinsonian drug" means a drug known in the art for use in treating Parkinson's disease.

Amantadine is also indicated and can be administered for the treatment of elderly patients believed to develop Parkinsonism in association with or as a result of cerebral arteriosclerosis or another neurodegenerative disease (Rajrut A H et al., *Parkinsonism Relat Disord* (1997), 3(4):211-4), dementia in Parkinson's disease (Inzelberg R et al., *Mov Disord* (2006), 21(9):1375-9), fatigue associated with multiple sclerosis (Krupp L B et al., *Neurology* (1995), 45:1956-1961), reducing relapses in multiple sclerosis (Plaut G S, *J R Soc Med* (1987 February), 80(2):91-3), improving symptoms of attention deficit hyperactivity disorder (ADHD) (Mohammadi M R et al., *Hum Psychopharmacol* (2010), 25(7)560-5), SSRI-induced sexual dysfunction (Shrivastava R K et al., *J Clinical Psychopharma* (1995), 15(1):83-84), management of addictions and substance dependence (Kampman K M et al., *Am J Psychiatry* (2000), 157:2052-2054), resistant unipolar depression (Rogoz Z et al. *Pharmacological Reports* (2007), 59(6):778-784), bipolar disorders (Ohlmeier M D et al., *Aust N Z J Psychiatry* (2007), 41(2):194), Alzheimer's Disease (Erkulwater S and Pillai R, *South Med J* (1989), 82(5):550-4), senile dementia (Müller H F et al., *J Am Geriatr Soc* (1979), 27(1):9-16), Huntington's disease (Bonelli R M and Wenning G K, *Curr Pharm Des* (2006), 12(21):2701-20), neuropathic pain (Amin P and Sturrock N D, *Diabet Med* (2003), 20(2):114-8), postoperative pain (Bujak-Giżycka B et al., *Pain Med* (2012), 13(3):459-65), refractory absence seizures (Perry M S et al., *Pediatr Neurol* (2012), 46(4):243-5), brain injury (Meyer M J et al., *Brain Inj* (2010), 24(5):722-9), and traumatic brain injury (Giacino J T et al., *N Engl J Med* (2012), 366:819-826).

Amantadine can also be administered for the management of impulse control disorders (impulsive behavior), such as pathological gambling and compulsive sexual behavior, compulsive behaviors, such as binge eating, compulsive shopping, overspending and excessive computer use, among individuals taking dopamine agonist medications for Parkinson's Disease (Weintraub D et al., *Arch Neurol* (2006), 63(7):969-973).

When the osmotic device of the invention is indicated for any one of the conditions, diseases or disorders disclosed herein, it can be administered according to the following protocol. A subject is diagnosed with one or more of the conditions, diseases or disorders. The subject is evaluated by a clinician, who prescribes an osmotic device according to the invention. The dose of amantadine to be administered to the subject will be determined by the clinician. Dosage and administration of the amantadine may follow any known dosing regimen.

Amantadine may be administered as a combination with one or more compounds selected from the group consisting of levodopa alone or in combination with an aromatic-L-amino-acid decarboxylase inhibitor such as carbidopa or benserezide; dopamine agonists such as apomorphine, bromocriptine, cabergoline, lisuride, pergolide, pramipexole, ropinirole, and rotigotine; COMT (catechol O-methyltransferase) inhibitors such as entacapone, tolcapone and BIA 9-1067 (opicapone); MAO-B (monoamine oxidase B) inhibitors such as selegiline, rasagiline and safinamide; anticholinergics such as trihexyphenidyl, benztropine, orphenadrine, procyclidine, ethopropazine, and glycopyrrolate; benzodiazepines such as alprazolam, lorazepam, diazepam, clonazepam; SSRIs (selective serotonin reuptake inhibitors) such as fluoxetine, sertraline, paroxetine and fluvoxamine; tricyclic and tetracyclic antidepressants such as mirtazapine, doxepin, imipramine, desipramine, trazodone, and nortriptyline; nonsteroidal anti-inflammatory agents such as minocycline and COX-2 (cyclooxygenase-2) inhibitors; non-narcotic analgesic such as acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol and zomepiracadenosine; narcotic analgesics such as codeine, dihydrocodeine, hydrocodone, hydromorphone, levorphanol, morphine, oxycodone and tapentadol; ADORA2A (adenosine A2A receptor) antagonists such as preladenant, tozadenant, DT-1133 and DT1687; anti-epileptic agents selected from the group consisting of AMPA antagonists, Benzodiazepines, Barbiturates, Valproates, GABA analogs, Iminostilbenes, Hydantoins, NMDA antagonists, Sodium channel blockers, Carboxylic acids, oxazolidinediones, succinimides, pyrrolidines, sulphonamides, aminobutyric acids, sulfamate-substituted monosaccharides, carboxamides, aromatic allylic alcohols, ureas, phenyltriazines, carbamates, pyrrolidines, losigamone, retigabine, rufinamide, acetazolamide, clomthiazole edisilate, zonisamide, felbamate, topiramate, tiagabine, levetiracetam, briveracetam, SPD 421 (DP-VPA), T-2000, XP-13512, GSK-362115, GSK-406725, ICA-69673, CBD cannabis derivative, isovaleramide (NPS-1776), carisbamate, safinamide, seletracetam, soretolide, stiripentol, and valrocemide; lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, ginkgo biloba, nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-B-hydroxyepiandrosterone, (+)-phenserine, clavulanic acid, HE-3286, YM-50018, MCD-386, AV-101, SUVN-502, EVP-0334, V-81444, SCH-900800, ADX-88178, NNZ-2591, AEOL-11207, Proximagen, IC-200214, SIG-1012, ADL-5510, TrkB PAM, and G-79.

When a drug other than amantadine is included in the osmotic device, it is present in an amount known to be therapeutically (clinically) effective for the treatment of a target condition, disease or disorder, such as those described herein, when a unit dose of the osmotic device is administered to a subject in need thereof. Guidance as to the therapeutically effective amount of each drug can be obtained from the Food and Drug Administration (USA, www.fda.gov), European Medicines Agency (Europe, ema.europa.eu), National Institute of Health Sciences (Japan, www.nihs.go.jp), and National Administration of Drugs, Food, and Medical Technology (Administración Nacional de Medicamentos, Alimentos y Tecnología Médica, Argentina, www.anmat.gov.ar), the disclosures of which are incorporated herein by reference in their entirety. For example, the package insert for any approved drug includes dosage and administration information, which can be used to determine the proper amount of each drug to be included in an osmotic device of the invention. The amounts for a particular drug combination in accordance with this invention can be determined employing routine experimental testing. If the drugs are present in such a weight ratio that a super-additive or synergistic therapeutic effect is observed upon administration to the patients, the overall administered dose may be lowered, so that fewer undesired side-effects will occur.

An osmotic device containing a combination of amantadine and one or more other drugs may contain an excess of amantadine, an excess of the one or more other drugs or equivalent amounts of amantadine and the one or more other drugs. The weight ratio of amantadine to the one or more other drugs can range from about 100:1 to 1:100. If necessary, the one or more other drugs can also be administered to the subject in another dosage form such that the subject receives a dose of the one or more other drugs in the osmotic device and a dose of the one or more other drugs in another dosage form. The dosing regimen for the one or more other drugs can thus be the same as or different than the dosing regimen for amantadine.

In some embodiments, the osmotic device comprises an external coat (a coat external to the semipermeable membrane) comprising a second active agent for immediate release of the drug. The external coat can be a rapid release coat. The second active ingredient in the external rapid release coat can be selected from the group consisting of amantadine, cabergoline, pergolide, selegiline, rasagiline, trihexyphenidyl, benztropine, donepezil, fluoxetine, sertraline, paroxetine, fluvoxamine, mirtazapine, doxepin, desipramine, clozapine, olanzapine, risperidone, aripiprazole, fludrocortisone, safinamide, and smilagenin.

When amantadine is present in the external coat and in the core, the total amount of amantadine in the osmotic device can range from 65-320 mg. The amount of amantadine in the core will generally exceed the amount present in the external coat. Accordingly, the amount of amantadine in the core will generally range from 50-85% of the total amount present in the osmotic device.

In a specific embodiment, the patient has Parkinson's disease, which, as used herein, also encompasses a diagnosis of parkinsonism. In one embodiment, the patient has early stage Parkinson's disease, and the amantadine is used as a monotherapy or in combination with a MAO-B inhibitor without concomitant use of levodopa. In another embodiment, the patient has late stage Parkinson's disease and the patient takes levodopa in addition to the amantadine. In another embodiment, the patient has multiple sclerosis and the amantadine is used for the treatment of fatigue.

In yet another embodiment, amantadine is combined with an active agent selected from narcotic analgesics, gabapentin and/or lacosamide to control a patient's pain. Examples of medical conditions and/or types of pain that can be treated with such an osmotic device include acute inflammatory pain; acute pain; alcoholism-associated or alcoholism-induced neuropathic pain; allodynia (occurring independently or as a symptom of another condition); arthritic conditions; back pain; cancer-related neuropathic pain, e.g., painful compression by tumor growth of adjacent nerves, the brain or the spinal cord; central neuropathic pain; chronic headache; chronic inflammatory pain; chronic pain; chronic pain due to peripheral nerve injury; diabetes-associated or diabetes-induced neuropathic pain; diabetic pain; diabetic distal sensory neuropathy; diabetic distal sensory polyneuropathy; fibromyalgia; headache; hyperalgesia (occurring independently or as a symptom of another condition); hyperesthesia; hyperpathia; migraine, including classical migraine and common migraine; myalgia; myofascial pain syndrome; neuralgia; neuroma; non-inflammatory musculoskeletal pain; non-inflammatory osteoarthritic pain; non-neuropathic inflammatory pain; neuropathic pain; pain associated with or induced by chemotherapy or radiation therapy; pain associated with or induced by traumatic nerve injury or compression or by traumatic injury to the brain or spinal cord; painful diabetic neuropathy; peripheral neuropathic pain; persistent clinical pain; phantom pain; rheumatoid arthritis pain; secondary inflammatory osteoarthritic pain; trigeminal neuralgia; and vascular headache.

In general, the use of the amantadine osmotic device will provide a method of treating or preventing a disorder, disease or symptom responsive to amantadine therapy, wherein there will be a lower incidence of adverse events compared to an amantadine immediate release dosage form (Example 5).

Three controlled-release osmotic amantadine formulations (T1, T2 and T3) were manufactured according to the Example 7. The controlled-release osmotic amantadine formulation T1 contains less than 6% of NaCl w/w, based upon the weight of the uncoated core, and more than 25% w/w of cellulose acetate grade 1, having 7-10% of hydroxyl groups and viscosity of 200-280 s, based upon the weight of the semipermeable membrane. The controlled-release osmotic amantadine formulation T2 contains more than 6% of NaCl w/w, based upon the weight of the uncoated core, and more than 25% w/w of cellulose acetate grade 1 based upon the weight of the semipermeable membrane. The controlled-release osmotic amantadine formulation T3 contains more than 6% of NaCl w/w, based upon the weight of the uncoated core, and less than 25% w/w of cellulose acetate grade 1 based upon the weight of the semipermeable membrane. The randomized, 4-ways crossover design disclosed in Example 8 was used to compare the relative bioavailability (extent of absorption) of the osmotic amantadine formulations, T1, T2 and T3 and a conventional immediate-release tablet (Symmetrel® of Endo Pharmaceuticals Inc.) under fasting conditions as the reference. Mean values of pharmacokinetics parameters of amantadine are shown in the following table.

| Parameter | Test | Geometric mean ratio Ref. | Test | Ratio (% Ref) |
|---|---|---|---|---|
| Cmax (ng/ml) | T1 | 554.4 | 373.2 | 67.32 |
|  | T2 | 554.4 | 345.2 | 62.26 |
|  | T3 | 554.4 | 206.7 | 37.28 |
| AUC 0-72 | T1 | 12639.9 | 10892.3 | 86.17 |
| (ng · h/ml) | T2 | 12639.9 | 9493.4 | 75.11 |
|  | T3 | 12639.9 | 6084.2 | 48.13 |
| AUCinf | T1 | 13076.4 | 11446.8 | 87.54 |
| (ng · h/ml) | T2 | 13076.4 | 10037.3 | 76.76 |
|  | T3 | 13076.4 | 6497.8 | 49.69 |

Surprisingly, the bioavailability of amantadine released from the instant osmotic device formulations T1, T2 and T3 varied according to the composition of the formulation. Bioavailability decreased in the following order: T1>T2>T3. Moreover, T2 and T3 yielded a mean bioavailability under the minimum desired bioavailability of 80% as compared to the reference product. T1 provided an amantadine bioavailability of about 87%, compared to the reference. Accordingly, the invention also provides a method of varying the bioavailability of amantadine released from an osmotic device comprising a core comprising amantadine salt and a salt having an ion in common and a semipermeable membrane surrounding the core and having a preformed aperture, the method comprising varying the weight ratio of amantadine salt to osmotic salt in the core and varying the weight percentage of cellulose acetate grade 1 to total weight of cellulose acetates present in the semipermeable membrane, wherein the semipermeable membrane comprises cellulose acetate grade 1, cellulose acetate grade 2, and plasticizer.

Three amantadine HCl osmotic device tablets (160 mg, 240 mg and 320 mg strengths of drug) were manufactured and comprised osmotic cores comprising 100 mg, 180 mg and 260 mg, respectively, of controlled release amantadine, and an external coating comprising 60 mg of immediate release amantadine, as described in Example 9. When administered to patients for the treatment of Parkinson's disease, the immediate and controlled release combination provides a therapeutic effect mainly during the waking day (period), starting with the first peak provided by the 60 mg immediate release phase, for a fast and effective control of the symptomatology. In a steady state, daily plasma concentrations will be kept within therapeutic levels providing the coverage of the expected therapeutic effect, allowing for a decrease of drug plasma concentrations during night hours thus avoiding significant cognitive side effects and sleep disturbances, which will be reverted with (overcome by) the IR component of the following dose administered.

The pharmacokinetic parameters of the amantadine formulations disclosed in Example 9 were compared to a reference syrup product (Amantadine 320 mg Syrup, 50 mg/5 mL, manufactured by HiTech Pharmacal) after single dose administration as described in Example 10. Mean values of pharmacokinetics parameters of amantadine are shown in the following table.

| Parameter | Test* | Geometric mean ratio | | Ratio (% Ref) |
|---|---|---|---|---|
| | | Ref. | Test | |
| $C_{max}$ (ng/ml) | A | 887.56 | 311.86 | 35.14 |
| | B | 887.56 | 446.05 | 50.26 |
| | C | 887.56 | 626.94 | 70.64 |
| $AUC_{0\text{-}tlast}$ (ng · h/ml) | A | 17508.01 | 7354.17 | 42.00 |
| | B | 17508.01 | 11171.16 | 63.81 |
| | C | 17508.01 | 15939.3 | 91.04 |
| $AUC_{inf}$ (ng · h/ml) | A | 17992.43 | 7850 | 43.63 |
| | B | 17992.43 | 11741.37 | 65.26 |
| | C | 17992.43 | 16543.76 | 91.95 |

* A, B and C=amantadine HCl osmotic device tablets of 160 mg, 240 and 320 mg strengths respectively. Formulations A, B and C (containing 60 mg fixed dose of IR amantadine and different amounts of ER amantadine) exhibited a directly proportional response to changes of dose within the range of 160 to 320 mg.

$AUC_{0\text{-}\infty}$ levels of amantadine HCl osmotic device tablets of 160 mg, 240 mg, and 320 mg strengths were 43.63%, 65.26%, and 91.95% respectively compared with the reference product. The $C_{max}$ levels of amantadine HCl osmotic device tablets of 160 mg 240 mg and 320 mg strengths were significantly different than, e.g. 35.14%, 50.26% and 70.64%, respectively, the reference product.

The peak plasma level of amantadine following administration of the reference product was reached in around two hours. The peak plasma levels of amantadine following administration of formulations A, B and C were reached within about 6-8 hours after administration.

The following examples should not be considered exhaustive, but merely illustrative of only a few of the many embodiments contemplated by the present invention. The methods described herein can be followed to prepare osmotic devices according to the invention.

Example 1

Amantadine HCl osmotic device tablets of 200 mg strengths comprising coating A, and 0, 10, 15 and 20% of sodium chloride in the core, and amantadine HCl osmotic device tablets of 200 mg strengths comprising coating B and 10, and 20% of sodium chloride in the core were manufactured with the following general method. Amantadine hydrochloride (200 mg), a diluent (70-200 mg), and a binder (18-30 mg), were first individually screened to a uniform size using a Quadro Comil at less than 1,000 rpm, and then mixed with sodium chloride previously milled using a Fitz Mill with a screen 0020-0069 at less than 8000 rpm, in a mixer granulator for up to 25 minutes to form a homogenous powder blend. The granulation process was initiated by the gradual addition of purified water to the powder blend, with continuous mixing, to change the consistency of the dry powder ingredients to granules. The wet granulation was sieved through a Quadro Comil at a speed less than 1000 rpm, and then dried in a static bed at 50° C. for humidity reduction. Next, the dry granules are milled using a Quadro Comil with a screen R991μ at less than 2,000 rpm for size reduction. Then, a mixture of a glidant (0.2-5 mg) and a lubricant (1-7 mg), previously sieved through a 100 mesh screen, was added and mixed for about 15 minutes. The resulting mixture was compressed in a compressor with 8.0 mm diameter punches to form uncoated cores. The average weight of the uncoated cores was approximately between 300 to 500 mg.

Two coating compositions were prepared: coating composition A containing a cellulose ester (18.0-29.0 mg) and a plasticizer of low molecular weight (0.5-3 mg) in a blend of acetone and purified water, and coating composition B containing a mixture of two different cellulose esters (9.0-15.0 mg of each cellulose ester) and a plasticizer of low molecular weight (0.5-3 mg) in a blend of acetone and purified water. Part of the resulting uncoated cores containing 0, 5, 10 and 20% of sodium chloride were coated with coating composition A, and the rest of the cores containing 10 and 20% of sodium chloride were then coated with coating composition B. The membrane coating weighed approximately between 9.5 and 32.0 mg.

The membrane coating of each core was then perforated with laser equipment to form at least one passageway of 0.2-0.8 mm through the semipermeable coat.

In one embodiment, the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly (ethylene oxide); the cellulose ester is selected from the group consisting of cellulose acetate, cellulose acylate, cellulose fatty acid ester, and cellulose acetate phthalate; the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate; the lubricant is selected from the group consisting of calcium stearate, magnesium stearate, mineral oil, stearic acid, and zinc stearate; the diluent is selected from the group consisting of microcrystalline cellulose, lactose, sucrose, mannitol, cellulose, starch, sorbitol, dibasic calcium phosphate, and calcium carbonate; and the glidant is selected from the group consisting of colloidal silica, cornstarch, talc, calcium silicate, magnesium silicate, colloidal silicon, and silicon hydrogel.

Example 2

Amantadine HCl osmotic device tablets of 300 mg strengths were manufactured as described herein. The osmotic device tablets contain the following ingredients in the amounts indicated:

| Ingredients | Amount (mg) |
|---|---|
| Core | |
| Amantadine HCl | 300 |
| Diluent 1 | 20-110 |
| Binder | 15-30 |
| Glidant | 0.2-5 |
| Lubricant | 1-7 |
| Sodium Chloride | 0-150 |
| Diluent 2 | 20-60 |
| Osmopolymer | 0-45 |
| Coating | |
| Cellulose ester 1 | 0-50 |
| Cellulose ester 2 | 0-50 |
| Plasticizer | 0.5-3.0 |

Amantadine hydrochloride (300 mg), diluent 1 (20-110 mg), diluent 2 (20-60 mg), a binder (15-30 mg), and an Osmopolymer (0-45 mg) were first individually screened to a uniform size using a Quadro Comil at less than 500 rpm, and then mixed with sodium chloride (0-150 mg) previously milled using a Fitz Mill with a screen 0020-0069 at less than 8000 rpm, in a mixer granulator for up to 5 minutes to form a homogenous powder blend. The granulation process was initiated by the gradual addition of purified water to the powder blend, with continuous mixing, to change the consistency of the dry powder ingredients to granules. The wet granulation was sieved through a Quadro Comil at a speed less than 500 rpm, and then dried in a static bed at 50° C. for humidity reduction. Next, the dry granules were milled using a Quadro Comil with a screen R991µ at less than 2,000 rpm for size reduction. Then, a mixture of a glidant (0.2-5 mg) and a lubricant (1-7 mg), previously sieved through a 60 mesh screen, was added and mixed for about 5 minutes. The resulting mixture was compressed in a compressor with 10-12 mm diameter punches to form uncoated cores. The average weight of the uncoated cores was approximately between 300 to 500 mg.

A coating composition was prepared as follows: cellulose ester 1 (0-50 mg), cellulose ester 2 (0-50 mg) and a plasticizer of low molecular weight (0.5-3 mg) were blended in acetone and purified water. The blend was sprayed onto the uncoated cores to obtain coated cores. The membrane coating weighed approximately between 2.5 and 80.0 mg. The membrane coating of each core was then perforated with laser equipment to form at least one passageway of 0.2-0.8 mm through the semipermeable coat.

In one embodiment, the binder is selected from the group consisting of poly(vinylpyrrolidone), povidone, copolyvidone, sodium carboxymethylcellulose, alginic acid, poly(ethylene glycol), guar gum, polysaccharide, bentonite clay, sugar, poloxamer, collagen, albumin, gelatin, poly(propylene glycol), hydroxypropyl methylcellulose, and poly(ethylene oxide); the cellulose ester is selected from the group consisting of cellulose acetate, cellulose acylate, cellulose fatty acid ester, and cellulose acetate phthalate; the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate; the lubricant is selected from the group consisting of calcium stearate, magnesium stearate, mineral oil, stearic acid, and zinc stearate; the diluent is selected from the group consisting of microcrystalline cellulose, lactose, sucrose, mannitol, cellulose, starch, sorbitol, dibasic calcium phosphate, and calcium carbonate; and the glidant is selected from the group consisting of colloidal silica, cornstarch, talc, calcium silicate, magnesium silicate, colloidal silicon, and silicon hydrogel; and the osmopolymer is selected from the group consisting of poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, sodium carboxymethylcellulose, hydroxypropyl methylcellulose, polyethylene oxide, polymers of N-vinyl-lactams, polyoxyethylene-polyoxypropylene gels, polyoxy-butylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides.

Example 3

The osmotic device tablets of examples 1 or 2 containing citalopram HBr (5, 10 and 20 mg strength) in a drug-containing external coat are prepared following the general procedure. Citalopram hydrobromide, a film forming polymer, a disintegrant and plasticizer are added to the purified water to form the coating suspension. This suspension is sprayed onto the tablets in a perforated pan coater to obtain drug load coated tablets.

A finish coat comprising Opadry in purified water is applied onto the drug load coated tablets to obtain the amantadine controlled release-citalopram immediate release osmotic device tablets.

Example 4

The osmotic device tablets of examples 1 or 2 containing buspirone HCl (5, 7.5 and 15 mg strength) in a drug-containing external coat are prepared following the general procedure.

Buspirone hydrochloride, a film forming polymer, a disintegrant and plasticizer are added to the acetone to form the coating suspension. This suspension is sprayed onto the tablets in a perforated pan coater to obtain drug load coated tablets.

A finish coat comprising Opadry in purified water is applied onto the drug load coated tablets to obtain the amantadine controlled release-buspirone immediate release osmotic device tablets.

Example 5

A pharmacokinetic-pharmacodynamic, double-blind, active and placebo-controlled, randomized, crossover, multiple-dose study on amantadine CR in patients with Parkinson's disease with levodopa (L-Dopa) treatment-related fluctuations is performed. The objective of the study is to correlate amantadine pharmacokinetic profiles of each formulation at steady state and the clinical response to levodopa in patients experiencing motor fluctuations.

Amantadine IR, CR (100, 150, 200, 250 or 300 mg) or placebo are given daily on a morning dose, for a period of at least 7 days in which the steady state levels are achieved. No changes in patient's individual dose of levodopa/dopa decarboxylase inhibitor are performed and it is administered daily at the same time. Plasma concentrations of levodopa, its metabolites, and amantadine are measured at steady state and motor responses are quantified at periodic intervals using the motor part of the Unified Parkinson's Disease Rating Scale (UPDRS) and the Abnormal Involuntary Movement Scale (AIMS). Imaging of the nigrostriatal dopaminergic pathway with either PET (Positron Emission Tomography) or SPECT (Single Photon Emission Computed Tomography) methods are used to further quantify a correlation of Parkinson's disease severity with the PK-PD effects of amantadine. Amantadine known adverse events (Aes) are also evaluated to establish a PK/PD (Aes) correlation.

A population pharmacokinetic-pharmacodynamic model is used to relate plasma concentrations of amantadine and levodopa with clinical response. A dose-proportional relationship between a steady-state pharmacokinetic parameters of amantadine (AUC, Cmax, Cmin or % Fluctuation), and any of the following outcomes: UPDR Scale, AIMS, levodopa and its metabolite pharmacokinetic parameters, or Aes incidence or severity, are indicative of a systemic concentration-response relationship of amantadine IR or CR in PD patients and a significant evidence of effectiveness in improving motor fluctuations in a dose-related fashion or the improvement in the safety profile of the product.

Example 6

Amantadine HCl osmotic device tablets of 100, 150, and 300 mg strengths were manufactured as described herein. The osmotic device tablets contain the following ingredients in the amounts indicated:

| Ingredient | Amount (mg) | | |
|---|---|---|---|
| Core | | | |
| Amantadine HCl | 100 | 150 | 300 |
| Diluent 1 | 7-35 | 10-55 | 20-100 |
| Binder | 3-10 | 4.5-15 | 10-30 |
| Glidant | 0.1-2 | 0.2-3 | 0.2-5 |
| Lubricant | 0.3-3 | 0.5-5 | 1-7 |
| Sodium Chloride | 0-50 | 0-75 | 0-150 |
| Diluent 2 | 3-20 | 4.5-30 | 10-60 |
| First Coating | | | |
| Cellulose ester 1 | 0-20 | 0-25 | 0-50 |
| Cellulose ester 2 | 0-20 | 0-25 | 0-50 |
| Plasticizer | 0.2-1 | 0.3-2 | 0.5-3 |

Amantadine hydrochloride, diluent 1, diluent 2, and a binder, were first individually screened to a uniform size using a Quadro Comil at less than 500 rpm, and then mixed with sodium chloride previously milled using a Fitz Mill with a screen 0020-0069 at less than 8000 rpm, in a mixer granulator for up to 5 minutes to form a homogenous powder blend. The granulation process was initiated by the gradual addition of purified water to the powder blend, with continuous mixing, to change the consistency of the dry powder ingredients to granules. The wet granulation was sieved through a Quadro Comil at a speed less than 500 rpm, and then dried in a static bed at 50° C. for humidity reduction. Next, the dry granules were milled using a Quadro Comil with a screen R991µ at less than 2,000 rpm for size reduction. Then, a mixture of a glidant and a lubricant, previously sieved through a 60 mesh screen, was added and mixed for about 5 minutes. The resulting mixture was compressed in a compressor with 7-10 mm diameter punches to form uncoated cores. The average core weight for the 100, 150, and 300 mg of the amantadine HCl osmotic device tablets are 150, 225 and 450 mg respectively.

A coating composition was prepared as follows: cellulose ester 1, cellulose ester 2, and a plasticizer of low molecular weight were blended in acetone and purified water. The blend was sprayed onto the uncoated cores to obtain coated cores. The membrane coating weighed approximately between 8 and 20 mg. The membrane coating of each core was then perforated with laser equipment to form at least one passageway of 0.2-0.8 mm through the semipermeable coat.

In one embodiment, the binder is selected from the group consisting of poly(vinylpyrrolidone), povidone, copolyvidone, sodium carboxymethylcellulose, alginic acid, poly(ethylene glycol), guar gum, polysaccharide, bentonite clay, sugar, poloxamer, collagen, albumin, gelatin, poly(propylene glycol), hydroxypropyl methylcellulose, and poly(ethylene oxide); the cellulose ester is selected from the group consisting of cellulose acetate, cellulose acylate, cellulose fatty acid ester, and cellulose acetate phthalate; the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate; the lubricant is selected from the group consisting of calcium stearate, magnesium stearate, mineral oil, stearic acid, and zinc stearate; the diluent is selected from the group consisting of microcrystalline cellulose, lactose, sucrose, mannitol, cellulose, starch, sorbitol, dibasic calcium phosphate, and calcium carbonate; and the glidant is selected from the group consisting of colloidal silica, cornstarch, talc, calcium silicate, magnesium silicate, colloidal silicon, and silicon hydrogel.

Example 7

Three amantadine HCl osmotic device tablets of 300 mg strength, formulations T1, T2 and T3, were manufactured as described in Example 6. The controlled-release osmotic amantadine formulation T1 contains less than 6% of NaCl w/w, based upon the weight of the uncoated core, and more than 25% w/w of cellulose acetate grade 1, having 7-10% of hydroxyl groups and viscosity of 200-280 s, based upon the weight of the semipermeable membrane. The controlled-release osmotic amantadine formulation T2 contains more than 6% of NaCl w/w, based upon the weight of the uncoated core, and more than 25% w/w of cellulose acetate grade 1 based upon the weight of the semipermeable membrane. The controlled-release osmotic amantadine formulation T3 contains more than 6% of NaCl w/w, based upon the weight of the uncoated core, and less than 25% w/w of cellulose acetate grade 1 based upon the weight of the semipermeable membrane.

Figure 8:
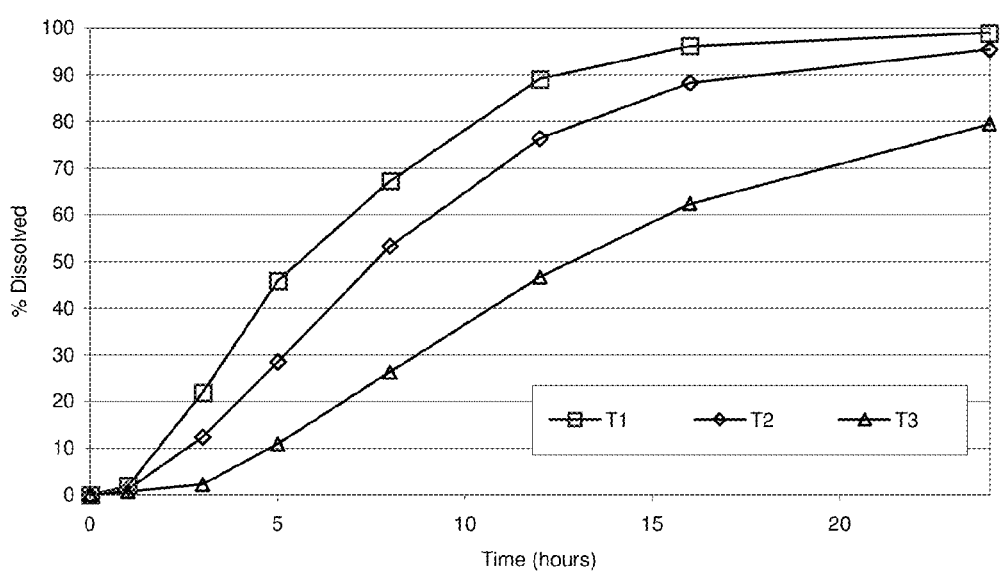
FIG. 8 depicts the in vitro release profiles of amantadine released from the exemplary formulations T1, T2 and T3 of Example 7.

The average in vitro release profile obtained for 12 tablets for T1 formulation is disclosed in the table below, and in FIG. 8. The performance minimum and performance maximum represent release profiles for the approximate lower and upper limits, respectively, for release of amantadine HCl over a larger range of formulations T1.

| Time (hrs) | Average (%) | SD (%) | Avg. Min (%) | Avg. Max (%) | Perform. Minimum (%) | Perform. Maximum (%) |
|---|---|---|---|---|---|---|
| 1 | 1.9 | 1.0 | 0.0 | 3.8 | 0 | 4 |
| 3 | 21.9 | 1.6 | 18.2 | 24.1 | 16 | 27 |
| 5 | 45.8 | 4.2 | 38.9 | 51.1 | 35 | 59 |
| 8 | 67.3 | 4.0 | 61.1 | 72.3 | 55 | 83 |
| 12 | 89.1 | 2.5 | 85.7 | 93.3 | 77 | 100 |
| 16 | 96.1 | 2.2 | 93.3 | 102.0 | 84 | 100 |
| 24 | 99.0 | 2.9 | 95.2 | 105.7 | 86 | 100 |

The average in vitro release profile obtained for 12 tablets for T2 formulation is disclosed in the table below, and in FIG. 8. The performance minimum and performance maximum represent release profiles for the approximate lower and upper limits, respectively, for release of amantadine HCl over a larger range of formulations T2 according to the invention.

| Time (hrs) | Average (%) | SD (%) | Avg. Min (%) | Avg. Max (%) | Perform. Minimum (%) | Perform. Maximum (%) |
|---|---|---|---|---|---|---|
| 1  | 1.2  | 1.0 | 0.3  | 3.9  | 0  | 4   |
| 3  | 12.3 | 3.9 | 6.0  | 18.4 | 5  | 20  |
| 5  | 28.4 | 6.0 | 19.9 | 37.4 | 18 | 43  |
| 8  | 53.3 | 6.4 | 43.8 | 63.2 | 39 | 73  |
| 12 | 76.3 | 5.3 | 68.6 | 85.7 | 62 | 99  |
| 16 | 88.3 | 2.6 | 84.3 | 93.0 | 76 | 100 |
| 24 | 95.4 | 1.5 | 93.1 | 98.1 | 84 | 100 |

The average in vitro release profile obtained for 12 tablets for T3 formulation is disclosed in the table below, and in FIG. 8. The performance minimum and performance maximum represent release profiles for the approximate lower and upper limits, respectively, for release of amantadine HCl over a larger range of formulations T3 according to the invention.

| Time (hrs) | Average (%) | SD (%) | Avg. Min (%) | Avg. Max (%) | Perform. Minimum (%) | Perform. Maximum (%) |
|---|---|---|---|---|---|---|
| 1  | 0.7  | 0.7  | 0.0  | 1.8  | 0  | 2   |
| 3  | 2.3  | 1.6  | 0.0  | 5.0  | 0  | 6   |
| 5  | 10.9 | 3.6  | 5.3  | 17.9 | 5  | 21  |
| 8  | 26.4 | 8.7  | 17.2 | 47.6 | 15 | 55  |
| 12 | 46.7 | 12.1 | 32.2 | 72.8 | 29 | 84  |
| 16 | 62.4 | 13.0 | 47.0 | 90.8 | 42 | 100 |
| 24 | 79.5 | 7.9  | 68.6 | 94.2 | 62 | 100 |

Example 8

A randomized, 4-ways crossover design was used to compare the relative bioavailability (extent of absorption) of three controlled-release osmotic amantadine formulations (T1, T2 and T3, 300 mg once-a-day) manufacture according to the Example 7, and a conventional immediate-release tablet (Symmetrel 100 mg, t.i.d) under fasting conditions as the reference. Twenty healthy subjects were recruited and randomly assigned to any of the 4 sequences according to the following scheme.

| Sequence | Period I | Period II | Period III | Period IV |
|---|---|---|---|---|
| 1 | R  | T3 | T1 | T2 |
| 2 | T1 | R  | T2 | T3 |
| 3 | T2 | T1 | T3 | R  |
| 4 | T3 | T2 | R  | T1 |

Blood samples were obtained prior dose and after administration at 0.5, 1, 1.5, 2, 3, 5, 8, 8.5, 9, 9.5, 10, 11, 13, 16, 16.5, 17, 17.5, 18, 19, 21, 24, 30, 36, 48, 72 hours for drug content analysis. Samples of 17 out of 20 subjects (1748 samples) who completed the four periods were analyzed by GC-MS for amantadine.

The pharmacokinetic parameters were estimated from concentration-time data using WinNonlin™ Professional, version 4.0 software.

Statistical analysis was carried out by using WinNonlin™ Professional, version 4.0 software. Log-transformed (natural logarithms) pharmacokinetic parameters $C_{max}$, AUClast and AUCinf, were evaluated by analysis of variance (ANOVA).

Example 9

Amantadine HCl osmotic device tablets containing amantadine in the core and amantadine in an external coat were manufactured as described herein. The osmotic device tablets contain the following ingredients in the amounts indicated:

| Ingredient | Amount (mg) | | | | |
|---|---|---|---|---|---|
| Amantadine HCl Strengths | 65-95 | 97.5-142.5 | 160 | 240 | 320 |
| Core | | | | | |
| Amantadine HCl | 50-65 | 75-97.5 | 100 | 180 | 260 |
| First Diluent | 7-34 | 12-50 | 10-42 | 20-67 | 30-106 |
| Binder | 2-6 | 4-14 | 3-12 | 4.5-22 | 10-30 |
| Glidant | 0.1-2 | 0.1-2.5 | 0.1-2 | 0.2-3 | 0.3-4 |
| Lubricant | 0.25-2.5 | 0.4-4.5 | 0.3-3 | 0.5-5 | 1-7 |
| Sodium Chloride | 0-40 | 0-60 | 0-50 | 0-75 | 0-150 |
| Second Diluent | 2-16 | 4-24 | 3-20 | 4.5-30 | 10-60 |
| First Coating (semipermeable membrane) | | | | | |
| Cellulose ester 1 | 0-20 | 0-20 | 0-20 | 0-25 | 0-25 |
| Cellulose ester 2 | 0-20 | 0-20 | 0-20 | 0-25 | 0-25 |
| Plasticizer | 0.2-2 | 0.2-2 | 0.2-2 | 0.3-3 | −0.4-4 |
| Inert Coating (optional coating) | | | | | |
| Film forming polymer | 5-10 | 5-10 | 5-10 | 5-15 | 7-20 |
| Second Coating (drug-containing coating exterior to semipermeable membrane) | | | | | |
| Amantadine HCl | 15-30 | 22.5-45 | 60 | 60 | 60 |
| Film forming polymer | 10-15 | 10-15 | 5-25 | 5-25 | 5-25 |

Although the table above names classes of compounds, any of such compounds disclosed herein, or known in the pharmaceutical sciences as being of such class, may be employed according to the invention provided the resulting osmotic device exhibits the desired sigmoidal release profile.

Amantadine hydrochloride, diluent 1 and a binder, were first individually screened to a uniform size using a Quadro Comil at less than 500 rpm, and then mixed with sodium chloride previously milled using a Fitz Mill with a screen 0020-0033 at less than 8500 rpm, in a mixer granulator for up to 5 minutes to form a homogenous powder blend. The granulation process was initiated by the gradual addition of the copovidone dissolved in purified water to the powder blend, with continuous mixing, to change the consistency of the dry powder ingredients to granules. The wet granulation was sieved through a Quadro Comil at a speed less than 500 rpm, and then dried in a fluid bed at 50° C. for humidity reduction. Next, the dry granules were milled using a Quadro Comil with a screen R991µ at less than 2,000 rpm for size reduction. Then, diluent 2 was added and mixed for 15 minutes. Next, a mixture of a glidant and a lubricant, previously sieved through a 40 mesh screen, was added and mixed for about 5 minutes. Finally, the resulting mixture was compressed in a rotatory press with 7-10.5 mm diameter punches to form uncoated cores. The average core weight for the 100, 180, and 260 mg of the amantadine HCl osmotic device tablets are 150, 270 and 390 mg respectively.

A first coating composition was prepared as follows: cellulose ester 1, cellulose ester 2, and a plasticizer of low molecular weight were dissolved in acetone and purified water. The solution was sprayed onto the uncoated cores in a Vector pan coater set up according to the following parameters: inlet temperature about 65° C., exhaust temperature about 32° C., airflow about 20 cfm, pan speed about 16 rpm, gun to bed distance about 8 cm, pump speed about 20 rpm, and spray rate about 20 g/min. The semipermeable membrane weight gain was approximately between 8 and 20 mg. The coated tablets were then perforated with laser equipment to form at least one passageway of 0.2-0.8 mm through the semipermeable membrane.

The inert coating composition was prepared by adding the film forming polymer into purified water under constant stirring to obtain a homogenous suspension. The solution was sprayed onto the coated cores in a Vector pan coater set up according to the following parameters: inlet temperature about 85° C., exhaust temperature about 38° C., airflow about 20 cfm, pan speed about 18 rpm, gun to bed distance about 9 cm, pump speed about 10 rpm, and spray rate about 10 g/min. The inert coating suspension was sprayed onto the tablets to a weight gain of approximately between 5-20 mg.

The second coating composition was prepared by dissolving amantadine hydrochloride into purified water under constant stirring. Then, the film forming polymer was added and mixed until a homogenous suspension was obtained. Finally, the solution was sprayed onto the coated cores in a Vector pan coater set up according to the following parameters: inlet temperature about 70° C., exhaust temperature about 38° C., airflow about 22 cfm, pan speed about 18 rpm, gun to bed distance about 9 cm, pump speed about 11 rpm, and spray rate about 20 g/min. The drug containing suspension was sprayed onto the tablets to an approximately weight gain between 50-100 mg.

Alternatively, the second coating can be prepared by mixing amantadine hydrochloride with a suitable binder and diluents and can be compressed about the first coating by a dry coating process using a rotator press machine equipped with 9 to 12 diameter punches to form the dry coated tablets.

Figure 9:
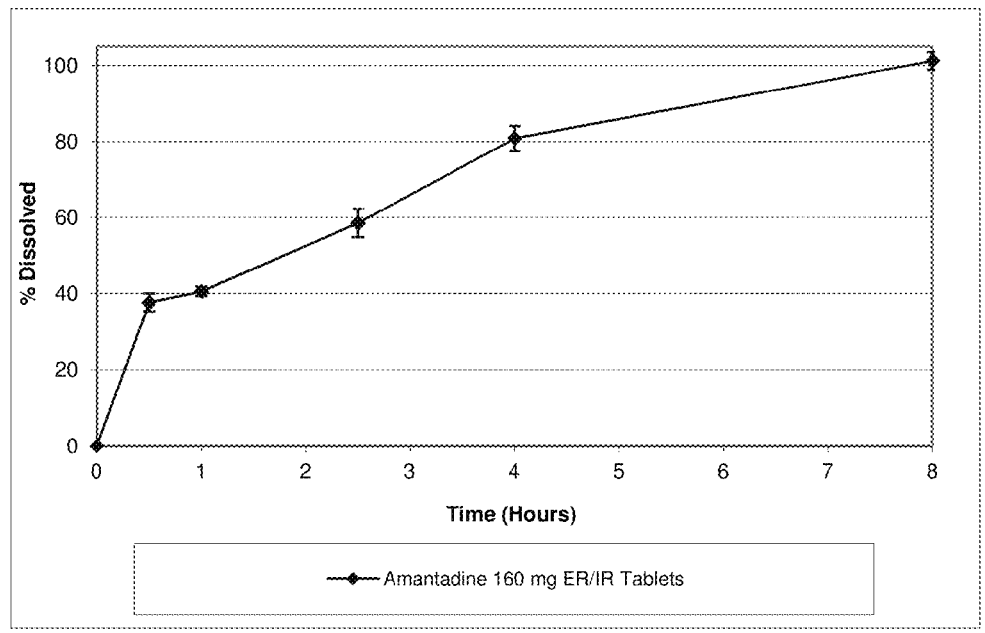
FIG. 9 depicts the in vitro release profile of amantadine released from the 160 mg strength amantadine HCl osmotic device tablets of Example 9.

The average in vitro release profile obtained for 6 tablets for the amantadine HCl osmotic device tablets of 160 mg strength is disclosed in the table below and in FIG. 9. The performance minimum and performance maximum represent release profiles for the approximate lower and upper limits, respectively, for release of amantadine HCl over a larger range of formulations.

| Time (hrs) | Average (%) | SD (%) | Avg. Min (%) | Avg. Max (%) | Performance Minimum (%) | Performance Maximum (%) |
|---|---|---|---|---|---|---|
| 0.5 | 37.6 | 2.4 | 34.7 | 41.0 | 0 | 50 |
| 1 | 40.5 | 1.2 | 39.1 | 42.5 | 25 | 55 |
| 2.5 | 58.5 | 3.7 | 53.0 | 62.6 | 45 | 75 |
| 4 | 80.8 | 3.3 | 76.8 | 85.6 | 65 | 95 |
| 8 | 101.2 | 2.3 | 98.0 | 104.8 | 85 | 100 |

Figure 10:
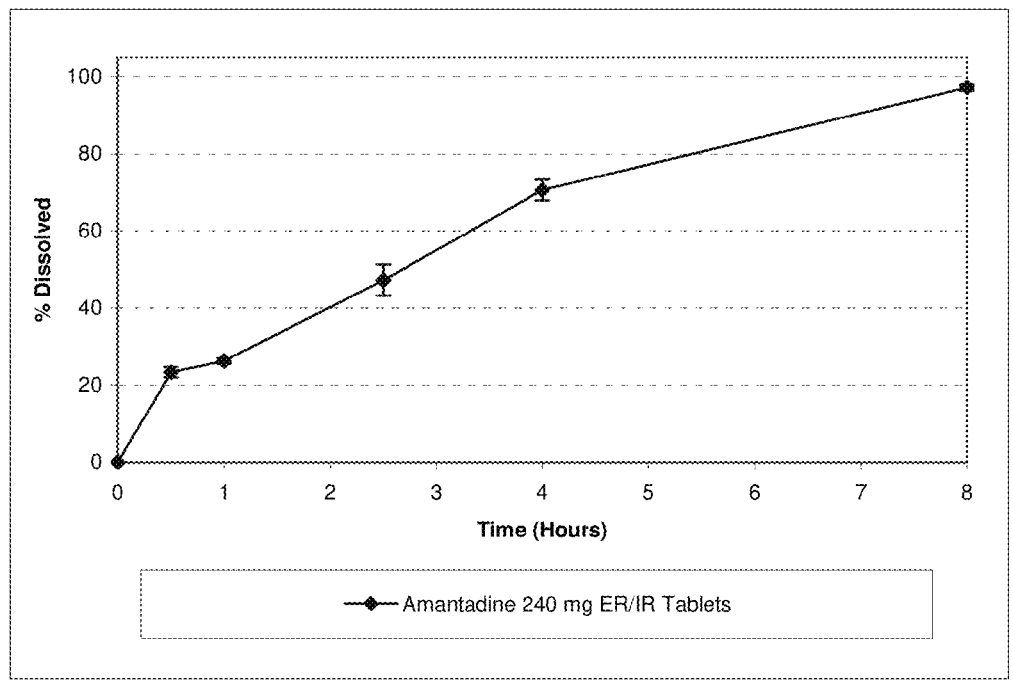
FIG. 10 depicts the in vitro release profile of amantadine released from the 240 mg strength amantadine HCl osmotic device tablets of Example 9.

The average in vitro release profile obtained for 6 tablets for the amantadine HCl osmotic device tablets of 240 mg strength is disclosed in the table below and in FIG. 10. The performance minimum and performance maximum represent release profiles for the approximate lower and upper limits, respectively, for release of amantadine HCl over a larger range of formulations.

| Time (hrs) | Average (%) | SD (%) | Avg. Min (%) | Avg. Max (%) | Performance Minimum (%) | Performance Maximum (%) |
|---|---|---|---|---|---|---|
| 0.5 | 23.3 | 1.4 | 21.6 | 25.3 | 0 | 40 |
| 1 | 26.2 | 0.7 | 25.1 | 26.9 | 10 | 40 |
| 2.5 | 47.3 | 4.0 | 41.1 | 52.1 | 30 | 60 |
| 4 | 70.6 | 2.7 | 66.8 | 74.5 | 55 | 85 |
| 8 | 97.2 | 0.8 | 95.9 | 98.0 | 80 | 100 |

Figure 11:
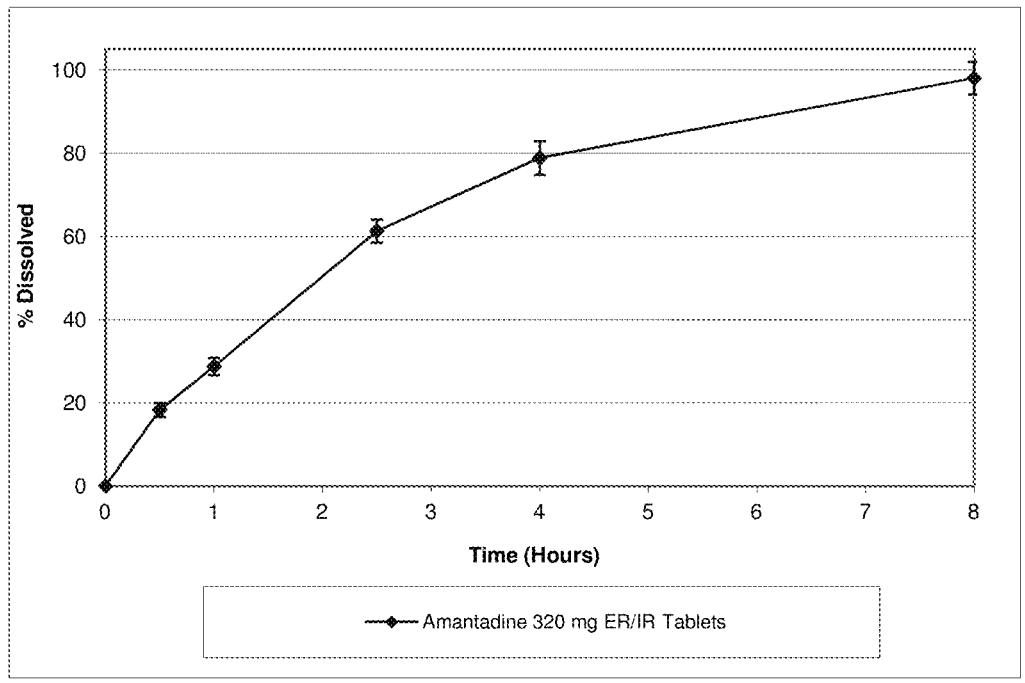
FIG. 11 depicts the in vitro release profile of amantadine released from the 320 mg strength amantadine HCl osmotic device tablets of Example 9.
Figure 12:
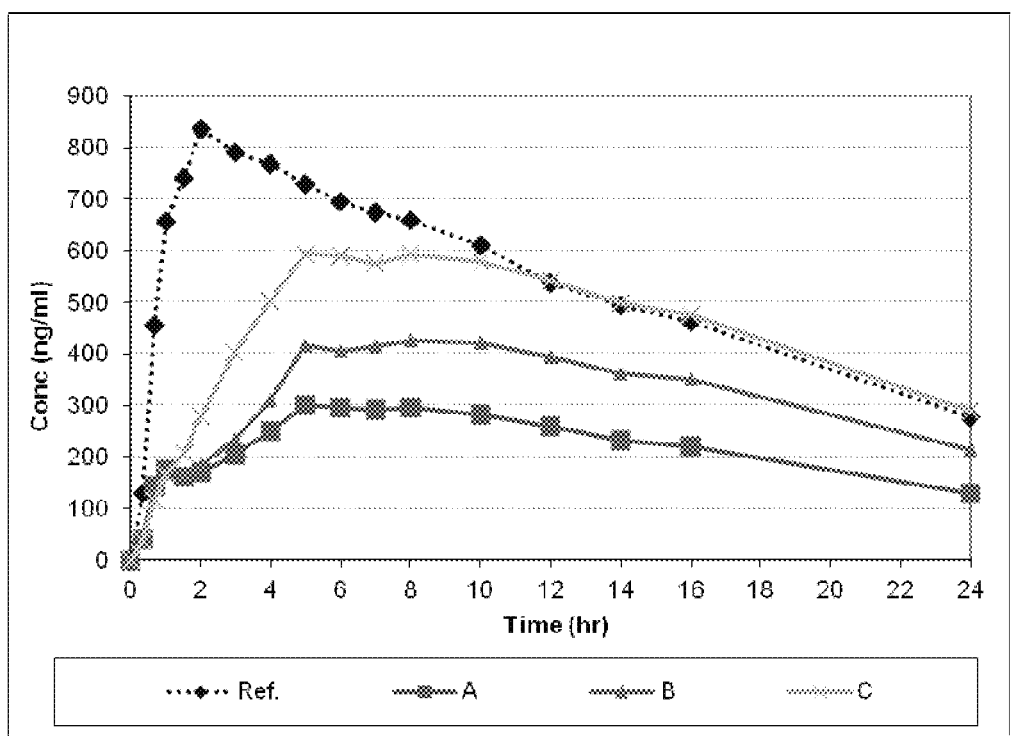
FIG. 12 depicts amantadine plasma concentration over a period of 24 hours following administration of a single dose of amantadine HCl osmotic device tablets of 160 mg (A), 240 mg (B) and 320 mg (C) strengths as disclosed in Example 10.

The average in vitro release profile obtained for 6 tablets for the amantadine HCl osmotic device tablets of 320 mg strength is disclosed in the table below and in FIG. 11. The performance minimum and performance maximum represent release profiles for the approximate lower and upper limits, respectively, for release of amantadine HCl over a larger range of formulations.

| Time (hrs) | Average (%) | SD (%) | Avg. Min (%) | Avg. Max (%) | Performance Minimum (%) | Performance Maximum (%) |
|---|---|---|---|---|---|---|
| 0.5 | 18.3 | 1.7 | 15.5 | 20.2 | 0 | 35 |
| 1 | 28.8 | 2.1 | 25.9 | 31.2 | 15 | 45 |
| 2.5 | 61.3 | 2.8 | 57.0 | 64.5 | 45 | 75 |
| 4 | 78.8 | 4.0 | 73.1 | 84.1 | 65 | 95 |
| 8 | 98.0 | 4.0 | 92.4 | 102.2 | 85 | 100 |

Example 10

A randomized, open label, single dose under fasting conditions, 4-way cross-over clinical trial was designed to evaluate the relationship between bioavailability and dose of amantadine HCl osmotic device tablets of 160 mg (A), 240 mg (B) and 320 mg (C) strengths disclosed in Example 9 versus a reference syrup formulation (Amantadine 320 mg Syrup, 50 mg/5 mL, manufactured by HiTech Pharmacal) in 24 healthy subjects.

All subjects were Caucasian males in a healthy state as judged by medical history, clinical examination as well as laboratory data. All subjects denied regular intake of medications within four weeks prior to the study as well as occasional intake within two weeks prior to the study. The subjects were randomly assigned to one of the different treatment sequences, separated by a wash-out period of seven (7) days between consecutive administrations of study medication. The subjects were randomly allocated to treatment sequences according to the treatment scheme below:

| Sequence | Period I | Period II | Period III | Period IV | N= |
|---|---|---|---|---|---|
| 1 | A | B | C | R | 6 |
| 2 | B | R | A | C | 6 |
| 3 | C | A | R | B | 6 |
| 4 | R | C | B | A | 6 |

Blood samples taken via an indwelling catheter or vein puncture from the forearm vein were obtained at pre-dose (collected at least 15 min prior to dosing, 00:00) and after administration at: 00:20; 00:40; 01:00; 01:30; 02:00; 03:00; 04:00; 05:00; 06:00; 07:00; 08:00; 10:00; 12:00; 14:00; 16:00; 24:00; 36:00; 48:00; 72:00; 96:00 hours. The amantadine plasma concentration was measured by LC-MS/MS.

All calculations of pharmacokinetic variables ($AUC_{0-tlast}$, $AUC_{0-\infty}$, $C_{max}$, $t_{max}$ and $t_{1/2}$) were carried out using specific commands of STATA-10 software. Pharmacokinetic parameters $AUC_{0-tlast}$, $AUC_{0-\infty}$ and $C_{max}$ of amantadine were tested parametrically for statistically significant differences by means of the ANOVA test procedure following logarithmical transformation of data.

Example 11

Amantadine HCl osmotic device tablets are manufactured as described in Example 6. Then, an optional inert coating composition is prepared by adding a film forming polymer into purified water under constant stirring to obtain a homogenous suspension. The solution is sprayed onto the coated cores in a Vector pan coater to obtain coated tablets. Next a second coating composition is prepared by dissolving or suspending a drug, and a film forming polymer and if necessary, any others suitable excipient such as solubilizing agents, stabilizers, buffering agents, plasticizers and/or antifoaming agents in a solvent or mixture of solvents and mixing until a homogenous suspension or solution is obtained. Examples of solvents comprise water, acetone, isopropanol, ethanol, methylene chloride and combinations thereof. Finally, the solution or suspension is sprayed onto the coated tablets in a Vector pan coater. Examples of drugs for the external drug-containing coat comprise amantadine, cabergoline, pergolide, selegiline, rasagiline, trihexyphenidyl, benztropine, donepezil, fluoxetine, sertraline, paroxetine, fluvoxamine, mirtazapine, doxepin, desipramine, clozapine, olanzapine, risperidone, aripiprazole, fluorocortisone, safinamide, dipraglurant, tozadenant, smilagenin and combinations thereof.

Example 12

Osmotic devices comprising a unitary core, a semipermeable membrane surrounding the core, a drug-containing coating exterior to the semipermeable membrane, and an optional inert, completely erodible or water soluble polymer coat partially or completely surrounding and in contact with the semipermeable membrane are made as describe above.

Method A. One Drug in Core and One or More Drugs in Drug-Containing Coating

Amantadine is included in the core, and one or more of the following classes of drugs is included in the drug-containing coating: anti-Parkinson drug, aromatic-L-amino-acid decarboxylase inhibitor, tricyclic antidepressant, tetracyclic antidepressant, anxiolytic agent, dopamine agonist, COMT inhibitor, MAO-B inhibitor, anticholinergic, benzodiazepine, SSRI, nonsteroidal anti-inflammatory agent, COX-2 (cyclooxygenase-2) inhibitor, non-narcotic analgesic, narcotic analgesic, A2A antagonist, anti-epileptic agent or another compound, such as those disclosed herein.

Alternatively, amantadine is included in the core, and one or more of the following drugs is included in the drug-containing coating: amantadine, buspirone, citalopram, diplagurant, levodopa, combination of levodopa and carbidopa, benserezide, apomorphine, bromocriptine, cabergoline, lisuride, pergolide, pramipexole, ropinirole, rotigotine; entacapone, tolcapone, BIA 9-1067 (opicapone), selegiline, rasagiline, safinamide; trihexyphenidyl, benztropine, orphenadrine, procyclidine, ethopropazine, glycopyrrolate, alprazolam, lorazepam, diazepam, clonazepam, fluoxetine, sertraline, paroxetine, fluvoxamine, mirtazapine, doxepin, imipramine, desipramine, trazodone, nortriptyline, minocycline, acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol zomepiracadenosine, codeine, dihydrocodeine, hydrocodone, hydromorphone, levorphanol, morphine, oxycodone, tapentadol, preladenant, tozadenant, DT-1133, DT1687, lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, ginkgo biloba (plant material or extract), nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-B-hydroxyepiandrosterone, (+)-phenserine, clavulanic acid, HE-3286, YM-50018, MCD-386, AV-101, SUVN-502, EVP-0334, V-81444, SCH-900800, ADX-88178, NNZ-2591, AEOL-11207, Proximagen, IC-200214, SIG-1012, ADL-5510, TrkB PAM, and G-79.

Method B. Two Drugs in Core and One or More Drugs in Drug-Containing Coating

Amantadine is included in the core, and one or more of the following classes of drugs is included in the core and in the drug-containing coating: anti-Parkinson drug, aromatic-L-amino-acid decarboxylase inhibitor, tricyclic antidepressant, tetracyclic antidepressant, anxiolytic agent, dopamine agonist, COMT inhibitor, MAO-B inhibitor, anticholinergic, benzodiazepine, SSRI, nonsteroidal anti-inflammatory agent, COX-2 (cyclooxygenase-2) inhibitor, non-narcotic analgesic, narcotic analgesic, A2A antagonist, anti-epileptic agent or another compound, such as those disclosed herein.

Alternatively, amantadine is included in the core, and one or more of the following drugs is included in the core and in the drug-containing coating: amantadine, buspirone, citalopram, diplagurant, levodopa, combination of levodopa and carbidopa, benserezide, apomorphine, bromocriptine, cabergoline, lisuride, pergolide, pramipexole, ropinirole, rotigotine; entacapone, tolcapone, BIA 9-1067 (opicapone), selegiline, rasagiline, safinamide; trihexyphenidyl, benztropine, orphenadrine, procyclidine, ethopropazine, glycopyrrolate, alprazolam, lorazepam, diazepam, clonazepam, fluoxetine, sertraline, paroxetine, fluvoxamine, mirtazapine, doxepin, imipramine, desipramine, trazodone, nortriptyline, minocycline, acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol zomepiracadenosine, codeine, dihydrocodeine, hydrocodone, hydromorphone, levorphanol, morphine, oxycodone, tapentadol, preladenant, tozadenant, DT-1133, DT1687, lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, ginkgo biloba (plant material or extract), nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-B-hydroxyepiandrosterone, (+)-phenserine, clavulanic acid, HE-3286, YM-50018, MCD-386, AV-101, SUVN-502, EVP-0334, V-81444, SCH- 900800, ADX-88178, NNZ-2591, AEOL-11207, Proximagen, IC-200214, SIG-1012, ADL-5510, TrkB PAM, and G-79

Method C. Two or More Drugs in Core

Amantadine is included in the core, and one or more of the following classes of drugs is included in the core: anti-Parkinson drug, aromatic-L-amino-acid decarboxylase inhibitor, tricyclic antidepressant, tetracyclic antidepressant, anxiolytic agent, dopamine agonist, COMT inhibitor, MAO-B inhibitor, anticholinergic, benzodiazepine, SSRI, nonsteroidal anti-inflammatory agent, COX-2 (cyclooxygenase-2) inhibitor, non-narcotic analgesic, narcotic analgesic, A2A antagonist, anti-epileptic agent or another compound, such as those disclosed herein.

Alternatively, amantadine is included in the core, and one or more of the following drugs is included in the core: buspirone, citalopram, diplagurant, levodopa, combination of levodopa and carbidopa, benserezide, apomorphine, bromocriptine, cabergoline, lisuride, pergolide, pramipexole, ropinirole, rotigotine; entacapone, tolcapone, BIA 9-1067 (opicapone), selegiline, rasagiline, safinamide; trihexyphenidyl, benztropine, orphenadrine, procyclidine, ethopropazine, glycopyrrolate, alprazolam, lorazepam, diazepam, clonazepam, fluoxetine, sertraline, paroxetine, fluvoxamine, mirtazapine, doxepin, imipramine, desipramine, trazodone, nortriptyline, minocycline, acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol zomepiracadenosine, codeine, dihydrocodeine, hydrocodone, hydromorphone, levorphanol, morphine, oxycodone, tapentadol, preladenant, tozadenant, DT-1133, DT1687, lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, ginkgo biloba (plant material or extract), nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-B-hydroxyepiandrosterone, (+)-phenserine, clavulanic acid, HE-3286, YM-50018, MCD-386, AV-101, SUVN-502, EVP-0334, V-81444, SCH-900800, ADX-88178, NNZ-2591, AEOL-11207, Proximagen, IC-200214, SIG-1012, ADL-5510, TrkB PAM, or G-79.

Example 13

The osmotic device of the invention is used to treat a condition, disease or disorder disclosed herein, or any other therapeutically responsive condition, disease or disorder, by administration thereof to a subject in need thereof. A subject is administered one or more osmotic devices at a time or throughout a 24-hour period in order to achieve the desired clinical benefit or therapeutic effect.

For the treatment of Parkinson's disease or Parkisonism of any kind, the daily dose of amantadine generally ranges from 200-400 mg. If another anti-Parkinson drug is included in the osmotic device, the daily for it generally ranges from 15-200 mg.

For the treatment of pain of any kind, the daily dose of amantadine generally ranges from 100-600, 200-500 or 200-400 mg. If analgesic, non-narcotic analgesic or NSAID is included in the osmotic device, the daily for it generally ranges from 25 to 1000 mg. If a narcotic analgesic is included in the osmotic device, the daily for it generally ranges from 50-800 mg. For the treatment of fatigue of any kind, the daily dose of amantadine generally ranges from 80-200 mg.

As used herein and unless otherwise specified, the term "about" or "approximately" are taken to mean±10%, ±5%, ±2.5% or ±1% of a specified valued. As used herein and unless otherwise specified, the term "substantially" is taken to mean "to a large degree", "at least a majority of", greater than 70%, greater than 85%, greater than 90%, greater than 95%, greater than 98% or greater than 99%.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

The invention claimed is:

1. An osmotic device comprising a unitary core surrounded by a semipermeable membrane having at least one passageway there through, wherein:
   a) the unitary core comprises a mixture of amantadine salt, osmotic salt, and at least one other pharmaceutically acceptable excipient, and the weight ratio of amantadine salt to osmotic salt ranges from 2:1 to 30:1;
   b) the osmotic salt is not coated with a release rate controlling coating;
   c) the permeability of the semipermeable membrane is adapted to cooperate with the osmotic salt to control the release profile of amantadine salt from the osmotic device;
   d) the amantadine salt and osmotic salt have an ion in common;
   e) amantadine salt is released through the one or more passageways according to a sigmoidal controlled release profile, optionally wherein release of amantadine salt is delayed for a period of time, when the osmotic device is exposed to an aqueous environment of use;
   f) the semipermeable membrane comprises a cellulose acetate grade 1 and a cellulose acetate grade 2, wherein the weight ratio of a cellulose acetate grade 1 to the total amount of cellulose acetates ranges from 0:1 to 1:1, wherein the cellulose acetate grade 1 comprises 7-10% by wt. of hydroxyl groups, 30-36% by wt. of acetyl groups and a viscosity of 200-280 seconds, and cellulose acetate grade 2 comprises 3-5% by weight of hydroxyl groups, 37-43% by wt. of acetyl groups and a viscosity of 6.0-45.0 seconds; and
   g) the osmotic device further comprises a drug-containing coat comprising an active ingredient, wherein the coat is external to the semipermeable membrane.

2. The osmotic device of claim 1 wherein:
the semipermeable membrane comprises 1.7%-15.0% by wt. of a plasticizer, 33.3%-61.2% by wt. of cellulose acetate grade 1, and 33.3%-61.2% by wt. of cellulose acetate grade 2, wherein the cellulose acetate grade 1 comprises 7-10% by wt. of hydroxyl groups, 30-36% by wt. of acetyl groups and has a viscosity of 200-280 seconds, and the cellulose acetate grade 2 comprises 3-5% by weight of hydroxyl groups, 37-43% by wt. of acetyl groups and has a viscosity of 6.0-45.0 seconds.

3. The osmotic device of claim 2, wherein the device further comprises an inert, completely erodible or water soluble polymer coat partially or completely surrounding and in contact with the semipermeable membrane, and the drug-containing coat is external to the inert polymer coat.

4. The osmotic device of claim 2, wherein the amantadine salt is an inorganic salt.

5. The osmotic device of claim 4, wherein the amantadine salt is a mineral acid salt.

6. The osmotic device of claim 4, wherein the amantadine salt is amantadine hydrochloride.

7. The osmotic device of claim 2, wherein the osmotic salt is a metal halide.

8. The osmotic device of claim 7, wherein the osmotic salt is an alkali metal halide or an earth metal halide.

9. The osmotic device of claim 7, wherein the osmotic salt is sodium chloride.

10. The osmotic device of claim 2, wherein the amantadine salt is amantadine hydrochloride and the osmotic salt is sodium chloride.

11. The osmotic device of claim 2, wherein the ion in common is chloride ion.

12. The osmotic device of claim 1, wherein the weight ratio of amantadine salt to osmotic salt ranges from 2:1 to 30:1, the osmotic device provides a sigmoidal release profile, and:
   a. the amount of osmotic salt in the core is <6% wt., the amount of cellulose acetate grade 1 in the semipermeable membrane is >25%, the ratio of cellulose acetate grade 1 to total amount of cellulose acetate in the semipermeable membrane is >0.25:1 or is 0.3:1 to 0.7:1;
   b. the amount of osmotic salt in the core is ≥6% wt., the amount of cellulose acetate grade 1 in the semipermeable membrane is ≤25%, the ratio of cellulose acetate grade 1 to total amount of cellulose acetate in the semipermeable membrane is <0.25:1; or
   c. the amount of osmotic salt in the core is ≥6% wt., the amount of cellulose acetate grade 1 in the semipermeable membrane is ≥25%, the ratio of cellulose acetate grade 1 to total amount of cellulose acetate in the semipermeable membrane is 0.25:1 to 0.4:1 or is 0.25:1 to 0.45:1.

13. The osmotic device of claim 2, wherein the active ingredient in the drug-containing coat is selected from the group consisting of an antidepressant, anxiolytic agent, anti-Parkinson drug, dopamine agonist, COMT inhibitor, MAO-B inhibitor, anticholinergic, benzodiazepine, SSRI, nonsteroidal anti-inflammatory agent, non-narcotic analgesic, narcotic analgesic, A2A antagonist, aromatic-L-amino-acid decarboxylase inhibitor, tricyclic antidepressant, tetracyclic antidepressant, dopamine agonist, and COX-2 inhibitor.

14. The osmotic device of claim 13, wherein the anti-Parkinson drug is selected from the group consisting of amantadine, selegiline, rasagiline, safinamide, diplagurant and tozadenant.

15. The osmotic device of claim 13, wherein the anti-Parkinson drug is amantadine.

16. The osmotic device of claim 2 further comprising a second active ingredient in the core.

17. The osmotic device of claim 16, wherein the second active ingredient in the core is selected from the group consisting of antidepressant, anxiolytic agent, anti-Parkinson drug, dopamine agonist, COMT inhibitor, MAO-B inhibitor, anticholinergic, benzodiazepine, SSRI, nonsteroidal anti-inflammatory agent, non-narcotic analgesic, narcotic analgesic, A2A antagonist, aromatic-L-amino-acid decarboxylase inhibitor, tricyclic antidepressant, tetracyclic antidepressant, dopamine agonist, and COX-2 inhibitor.

18. The osmotic device of claim 17, wherein the anti-Parkinson drug in the core is selected from the group consisting of ropinirole, selegiline, diplagurant, tozadenant, levodopa and a combination of levodopa-carbidopa.

19. The osmotic device of claim 17, wherein the narcotic analgesic in the core is selected from the group consisting of codeine, dihydrocodeine, hydrocodone, hydromorphone, levorphanol, morphine, oxycodone and tapentadol.

20. The osmotic device of claim 2, wherein the amantadine salt is released from the core according to a sigmoidal release profile as follows:

| Time (hours) | Amount Released |
| --- | --- |
| 0-3 | Not less than 5% |
| 0-5 | Not less than 18% |
| 0-8 | Not less than 39% |
| 0-16 | Not less than 76%. |

21. The osmotic device of claim 2, wherein the amantadine is released from the core according to the following sigmoidal release profile:

| Time (hrs) | Performance Minimum (%) | Performance Maximum (%) |
| --- | --- | --- |
| 0.5 | 0 | 50 |
| 1 | 25 | 55 |
| 2.5 | 45 | 75 |
| 4 | 65 | 95 |
| 8 | 85 | 100. |

22. The osmotic device of claim 2, wherein the amantadine is released from the core according to the following sigmoidal release profile:

| Time (hrs) | Performance Minimum (%) | Performance Maximum (%) |
| --- | --- | --- |
| 0.5 | 0 | 40 |
| 1 | 10 | 40 |
| 2.5 | 30 | 60 |
| 4 | 55 | 85 |
| 8 | 80 | 100. |

23. The osmotic device of claim 2, wherein the amantadine is released from the core according to the following sigmoidal release profile:

| Time (hrs) | Performance Minimum (%) | Performance Maximum (%) |
| --- | --- | --- |
| 0.5 | 0 | 35 |
| 1 | 15 | 45 |
| 2.5 | 45 | 75 |
| 4 | 65 | 95 |
| 8 | 85 | 100. |

24. The osmotic device of claim 15, wherein amantadine is released from the drug-containing coat in an immediate release manner.

25. The osmotic device of claim 1, wherein the weight ratio of amantadine salt to osmotic salt ranges from 4:1 to 30:1, and the semipermeable membrane comprises a weight ratio of a cellulose acetate grade 1 to the total amount of cellulose acetates from 0.3:1 to 0.7:1.

26. The osmotic device of claim 12, wherein the unitary core comprises less than 6% of NaCl w/w based upon the weight of the uncoated core, the semipermeable membrane comprises more than 25% w/w of cellulose acetate grade 1 based upon the weight of the semipermeable membrane, and the amantadine is released from the core according to the following sigmoidal release profile:

| Time (hrs) | Performance Minimum (%) | Performance Maximum (%) |
|---|---|---|
| 1 | 0 | 4 |
| 3 | 16 | 27 |
| 5 | 35 | 59 |
| 8 | 55 | 83 |
| 12 | 77 | 100 |
| 16 | 84 | 100 |
| 24 | 86 | 100. |

27. The osmotic device of claim 12, wherein the unitary core comprises 6% or more of NaCl w/w, based upon the weight of the uncoated core, and the semipermeable membrane comprises 25% w/w or more of cellulose acetate grade 1, based upon the weight of the semipermeable membrane, and the ratio of cellulose acetate grade 1 to the total amount of cellulose acetate in the semipermeable membrane is 0.25:1 to 0.45:1, and the amantadine is released from the core according to the following sigmoidal release profile:

| Time (hrs) | Performance Minimum (%) | Performance Maximum (%) |
|---|---|---|
| 1 | 0 | 4 |
| 3 | 5 | 20 |
| 5 | 18 | 43 |
| 8 | 39 | 73 |
| 12 | 62 | 99 |
| 16 | 76 | 100 |
| 24 | 84 | 100. |

28. The osmotic device of claim 12, wherein the unitary core comprises 6% or more of NaCl w/w, based upon the weight of the uncoated core, and the semipermeable membrane comprises 25% w/w or less of cellulose acetate grade 1, based upon the weight of the semipermeable membrane, and the ratio of cellulose acetate grade 1 to the total amount of cellulose acetate in the semipermeable membrane is 0.25:1 or less, and the amantadine is released from the core according to the following sigmoidal release profile:

| Time (hrs) | Performance Minimum (%) | Performance Maximum (%) |
|---|---|---|
| 1 | 0 | 2 |
| 3 | 0 | 6 |
| 5 | 5 | 21 |
| 8 | 15 | 55 |
| 12 | 29 | 84 |
| 16 | 42 | 100 |
| 24 | 62 | 100. |

29. The osmotic device of claim 2, wherein the unitary core comprises less than 6% of NaCl w/w, based upon the weight of the uncoated core.

30. The osmotic device of claim 29, wherein the amantadine is released from the core according to the following sigmoidal release profile:

| Time (hrs) | Performance Minimum (%) | Performance Maximum (%) |
|---|---|---|
| 1 | 0 | 4 |
| 3 | 16 | 27 |
| 5 | 35 | 59 |
| 8 | 55 | 83 |
| 12 | 77 | 100 |
| 16 | 84 | 100 |
| 24 | 86 | 100. |

31. The osmotic device of claim 2, wherein the unitary core comprises more than 6% of NaCl w/w, based upon the weight of the uncoated core.

32. The osmotic device of claim 31, wherein the amantadine is released from the core according to the following sigmoidal release profile:

| Time (hrs) | Performance Minimum (%) | Performance Maximum (%) |
|---|---|---|
| 1 | 0 | 4 |
| 3 | 5 | 20 |
| 5 | 18 | 43 |
| 8 | 39 | 73 |
| 12 | 62 | 99 |
| 16 | 76 | 100 |
| 24 | 84 | 100. |

33. The osmotic device of claim 1, wherein the core comprises:

| Ingredient | Amount (mg) |
|---|---|
| Core | |
| Amantadine HCl | 100 |
| First Diluent | 7-35 |
| Binder | 3-10 |
| Glidant | 0.1-2 |
| Lubricant | 0.3-3 |
| Sodium Chloride | 3.33-50 |
| Second Diluent | 3-20. |

34. The osmotic device of claim 1, wherein in the core comprises:

| Ingredient | Amount (mg) |
|---|---|
| Core | |
| Amantadine HCl | 150 |
| First Diluent | 10-55 |
| Binder | 4.5-15 |
| Glidant | 0.2-3 |
| Lubricant | 0.5-5 |
| Sodium Chloride | 5-75 |
| Second Diluent | 4.5-30. |

35. The osmotic device of claim 1, wherein the core comprises:

| Ingredient | Amount (mg) |
|---|---|
| Core | |
| Amantadine HCl | 300 |
| First Diluent | 20-100 |
| Binder | 10-30 |
| Glidant | 0.2-5 |
| Lubricant | 1-7 |
| Sodium Chloride | 10-150 |
| Second Diluent | 10-60. |

36. The osmotic device of claim 1 comprising any of the following formulations:

| Ingredient | Amount (mg) | | |
|---|---|---|---|
| | A | B | C |
| Amantadine HCl Strengths | 160 | 240 | 320 |
| Amantadine HCl | 100 | 180 | 260 |
| First Diluent | 10-42 | 20-67 | 30-106 |
| Binder | 3-12 | 4.5-22 | 10-30 |
| Glidant | 0.1-2 | 0.2-3 | 0.3-4 |
| Lubricant | 0.3-3 | 0.5-5 | 1-7 |
| Sodium Chloride | 0-50 | 0-75 | 0-150 |
| Second Diluent | 3-20 | 4.5-30 | 10-60 |
| First Coating (semipermeable membrane) | | | |
| Cellulose ester 1 | 0-20 | 0-25 | 0-25 |
| Cellulose ester 2 | 0-20 | 0-25 | 0-25 |
| Plasticizer | 0.2-2 | 0.3-3 | –0.4-4 |
| Inert Coating (optional coating) | | | |
| Film forming polymer | 0-10 | 5-15 | 7-20 |
| Second Coating (drug-containing coating exterior to semipermeable membrane) | | | |
| Amantadine HCl | 60 | 60 | 60 |
| Film forming polymer | 5-25 | 5-25 | 5-25 | wherein the total amount of cellulose acetate is greater than zero.

37. The osmotic device of claim 13 or 17, wherein the active ingredient in the drug-containing coat or the second active ingredient in the core is independently selected from the group consisting of amantadine, buspirone, citalopram, diplagurant, levodopa, combination of levodopa and carbidopa, benserezide, apomorphine, bromocriptine, cabergoline, lisuride, pergolide, pramipexole, ropinirole, rotigotine; entacapone, tolcapone, BIA 9-1067 (opicapone), selegiline, rasagiline, safinamide; trihexyphenidyl, benztropine, orphenadrine, procyclidine, ethopropazine, glycopyrrolate, alprazolam, lorazepam, diazepam, clonazepam, fluoxetine, sertraline, paroxetine, fluvoxamine, mirtazapine, doxepin, imipramine, desipramine, trazodone, nortriptyline, minocycline, acetaminophen, aspirin, diclofenac, diflusinal, etodolac, fenbufen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, tramadol zomepiracadenosine, codeine, dihydrocodeine, hydrocodone, hydromorphone, levorphanol, morphine, oxycodone, tapentadol, preladenant, tozadenant, DT-1133, DT1687, lacosamide, gabapentin, indomethacin, steroids, fluorocortisone, desmopressin, oxybutynin, tolterodine, hyoscyamine, midodrine, phenylephrine, phenylpropanolamine, baclofen, dantrolene, domperidone, mosapride, tegaserod, donepezil, memantine, riluzole, rivastigmine, coenzyme Q10, vitamin E, vitamin C, creatine, ginkgo biloba (plant material or extract), nicotinamide, carnitine, piribedil, buspirone, clozapine, quetiapine, olanzapine, risperidone, aripiprazole, methylphenidate, modafinil, dipraglurant, fipamezole, AFQ056, AQW-051, Neu-120, olesoxime, 17-β-hydroxyepiandrosterone, (+)-phenserine, clavulanic acid, HE-3286, YM-50018, MCD-386, AV-101, SUVN-502, EVP-0334, V-81444, SCH-900800, ADX-88178, NNZ-2591, AEOL-11207, Proximagen, IC-200214, SIG-1012, ADL-5510, TrkB PAM, and G-79.

38. A method of treating a condition, disease or disorder that is therapeutically responsive to amantadine therapy, comprising administering to a subject in need thereof an osmotic device according to any one of claims 2 or 12.

39. A method of treating a condition, disease or disorder that is therapeutically responsive to a combination of amantadine and a second active ingredient, comprising administering to a subject in need thereof an osmotic device according to any one of claims 2 or 12.

40. The method of claim 38, wherein the condition, disease or disorder is selected from the group consisting of Parkinson's disease, Parkinsonism, Parkinsonism associated with cerebral arteriosclerosis, Parkinsonism associated with neurodegenerative disease, dementia associated with Parkinson's disease, senile dementia, relapse in multiple sclerosis thereby providing a reduction thereof, drug-induced extrapyramidal reactions, viral infection, tremors, akinesia, dyskinesia, attention deficit hyperactivity disorder, SSRI-induced sexual dysfunction, levodopa induced dyskinesia, bradykinesia, impulse control disorder, addiction, substance dependence, resistant unipolar depression, bipolar disorder, pain, refractory absence seizure, bipolar disorder, Alzheimer's disease, Huntington's disease, amyotrophic lateral sclerosis, fatigue associated with multiple sclerosis, neurodegenerative disease, neuropathic pain, post-operative pain, refractory absence seizures, brain injury, traumatic brain injury, cerebrovascular condition, movement disorder, cranial nerve disorder, and neuropsychiatric disorders.

41. The method of claim 40, wherein the condition, disease or disorder is Parkinson's disease or Parkinsonism and the subject is administered: a) an osmotic device comprising amantadine as the sole drug or active ingredient; b) an osmotic device comprising amantadine as the sole drug or active ingredient and is concomitantly administered levodopa; or c) an osmotic device comprising amantadine and a MAO-B inhibitor without concomitant administration of levodopa to the subject.

42. The method of claim 40, wherein the condition, disease or disorder is fatigue associated with multiple sclerosis and the subject is administered an osmotic device comprising amantadine as the sole drug or active ingredient.

43. The method of claim 40, wherein the condition, disease or disorder is pain, and the subject is administered an osmotic device comprising amantadine and an active agent selected from the group consisting of a narcotic analgesic, gabapentin and lacosamide.

44. The method of claim 40, wherein the osmotic device provides a peak plasma level for amantadine within 6 to 8 hours after administration thereof to a subject.

45. The method of claim 44, wherein an osmotic device comprising 160 mg to 320 mg of amantadine provides an $AUC_\infty$ of about 6670 ng.h/ml to 19000 ng.h/ml for amantadine when administered once daily.

46. The method of claim 45, wherein the osmotic device provides a Cmax of about 265 ng/ml to 720 ng/ml when administered.

47. The method of claim 39, wherein the condition, disease or disorder is fatigue and the subject is administered an osmotic device comprising amantadine and baclofen.

48. The method of claim 47, wherein:
   a. the core comprises amantadine and baclofen;
   b. the core comprises amantadine and the drug-containing coat comprises baclofen;
   c. the core comprises amantadine, and the drug-containing coat comprises amantadine and baclofen; or
   d. the core comprises amantadine and baclofen, and the drug-containing coat comprises amantadine and baclofen.

49. The method of claim 48, wherein the osmotic device comprises 65 to 95 mg, 75 to 97.5 mg, 97.5 to 142.5 mg, about 75 to about 100 mg, 80 to 200 mg, 100 mg, 150 mg, 160 mg, 180 mg or 200 mg of amantadine or salt thereof.

50. The method of claim 39, wherein the condition, disease or disorder is attention deficit hyperactivity disorder and the subject is administered an osmotic device comprising amantadine and methylphenidate.

51. The method of claim 50, wherein:
   a. the core comprises amantadine and methylphenidate;
   b. the core comprises amantadine and the drug-containing coat comprises methylphenidate;
   c. the core comprises amantadine, and the drug-containing coat comprises amantadine and methylphenidate; or
   d. the core comprises amantadine and methylphenidate, and the drug-containing coat comprises amantadine and methylphenidate.

52. The method of claim 51, wherein the osmotic device comprises about 50 mg to about 75 mg, 65 to 320 mg or 100 to 600 mg of amantadine or salt thereof.

53. The method of claim 39, wherein the osmotic device comprises about 50 mg to about 75 mg, 65 to 320 mg or 100 to 600 mg of amantadine or salt thereof.

54. The method of claim 38, wherein the osmotic device comprises about 50 mg to about 75 mg, 65 to 320 mg or 100 to 600 mg of amantadine or salt thereof.

55. The osmotic device of claim 2, wherein the osmotic device comprises about 50 mg to about 75 mg, 65 to 320 mg or 100 to 600 mg of amantadine or salt thereof.

56. The osmotic device of claim 12, wherein the osmotic device comprises about 50 mg to about 75 mg, 65 to 320 mg or 100 to 600 mg of amantadine or salt thereof.

57. The osmotic device of claim 12, wherein the weight ratio of amantadine salt to osmotic salt ranges from 4:1 to 30:1.

58. The method of claim 52, wherein the osmotic device comprises about 50 to 65 mg, 65 to 95 mg, about 75 to about 100 mg, 80 to 200 mg, about 100 to about 300 mg, 160 to 320 mg or 200 to 500 mg of amantadine or salt thereof.

59. The method of claim 58, wherein the osmotic device comprises about 75 to 97.5 mg, 97.5 to 142.5 mg, 200 mg to 400 mg, 100 mg, 150 mg, 160 mg or 180 mg of amantadine or salt thereof.

60. The method of claim 59, wherein the osmotic device comprises 200 mg, 240 mg, 250 mg, 260 mg, 300 mg or 320 mg of amantadine or salt thereof.

61. The method of claim 53, wherein the osmotic device comprises about 50 to 65 mg, 65 to 95 mg, about 75 to about 100 mg, 80 to 200 mg, about 100 to about 300 mg, 160 to 320 mg or 200 to 500 mg of amantadine or salt thereof.

62. The method of claim 61, wherein the osmotic device comprises about 75 to 97.5 mg, 97.5 to 142.5 mg, 200 mg to 400 mg, 100 mg, 150 mg, 160 mg or 180 mg of amantadine or salt thereof.

63. The method of claim 62, wherein the osmotic device comprises 200 mg, 240 mg, 250 mg, 260 mg, 300 mg or 320 mg of amantadine or salt thereof.

64. The method of claim 54, wherein the osmotic device comprises about 50 to 65 mg, 65 to 95 mg, about 75 to about 100 mg, 80 to 200 mg, about 100 to about 300 mg, 160 to 320 mg or 200 to 500 mg of amantadine or salt thereof.

65. The method of claim 64, wherein the osmotic device comprises about 75 to 97.5 mg, 97.5 to 142.5 mg, 200 mg to 400 mg, 100 mg, 150 mg, 160 mg or 180 mg of amantadine or salt thereof.

66. The method of claim 65, wherein the osmotic device comprises 200 mg, 240 mg, 250 mg, 260 mg, 300 mg or 320 mg of amantadine or salt thereof.

67. The osmotic device of claim 55, wherein the osmotic device comprises about 50 to 65 mg, 65 to 95 mg, about 75 to about 100 mg, 80 to 200 mg, about 100 to about 300 mg, 160 to 320 mg or 200 to 500 mg of amantadine or salt thereof.

68. The osmotic device of claim 67, wherein the osmotic device comprises about 75 to 97.5 mg, 97.5 to 142.5 mg, 200 mg to 400 mg, 100 mg, 150 mg, 160 mg or 180 mg of amantadine or salt thereof.

69. The osmotic device of claim 68, wherein the osmotic device comprises 200 mg, 240 mg, 250 mg, 260 mg, 300 mg or 320 mg of amantadine or salt thereof.

70. The osmotic device of claim 56, wherein the osmotic device comprises about 50 to 65 mg, 65 to 95 mg, about 75 to about 100 mg, 80 to 200 mg, about 100 to about 300 mg, 160 to 320 mg or 200 to 500 mg of amantadine or salt thereof.

71. The osmotic device of claim 70, wherein the osmotic device comprises about 75 to 97.5 mg, 97.5 to 142.5 mg, 200 mg to 400 mg, 100 mg, 150 mg, 160 mg or 180 mg of amantadine or salt thereof.

72. The osmotic device of claim 71, wherein the osmotic device comprises 200 mg, 240 mg, 250 mg, 260 mg, 300 mg or 320 mg of amantadine or salt thereof.

* * * * *